(12) United States Patent
Gilligan et al.

(10) Patent No.: US 6,518,271 B1
(45) Date of Patent: Feb. 11, 2003

(54) 1H-IMIDAZO[4,5-D]PYRIDAZIN-7-ONE, AND CORRESPONDING THIONES AS CORTICOTROPIN RELEASING FACTOR (CRF) RECEPTOR LIGANDS

(75) Inventors: Paul Joseph Gilligan, Wilmington, DE (US); Rajagopal Bakthavatchalam, Wilmington, DE (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/634,784

(22) Filed: Aug. 9, 2000

Related U.S. Application Data

(62) Division of application No. 09/473,870, filed on Dec. 28, 1999, now Pat. No. 6,271,380.
(60) Provisional application No. 60/114,188, filed on Dec. 30, 1998.
(51) Int. Cl.[7] .................... A61K 31/495; A61K 31/50; C07D 401/00; C07D 403/00; C07D 235/02
(52) U.S. Cl. ............ 514/252.01; 514/303; 514/252.02; 544/236; 544/239; 548/300.1; 548/303.4
(58) Field of Search ................ 544/236, 238, 544/239; 514/252.01, 252.06, 303; 548/300.1, 303.4

(56) References Cited

FOREIGN PATENT DOCUMENTS

| EP | 0778277 A1 | 6/1997 |
| WO | 9119715 | * 12/1991 |
| WO | 9510506 | 4/1995 |
| WO | 9533727 | 12/1995 |
| WO | 9533750 | 12/1995 |
| WO | 9534563 | 12/1995 |
| WO | 0001697 | 1/2000 |

* cited by examiner

Primary Examiner—Richard L. Raymond
Assistant Examiner—Sudhaker R. Patel
(74) Attorney, Agent, or Firm—Christine A. Goddard

(57) ABSTRACT

Corticotropin releasing factor (CRF) antagonists of formula I:

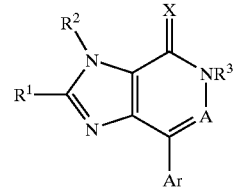

(1)

and their use in treating anxiety, depression, and other psychiatric, neurological disorders as well as treatment of immunological, cardiovascular or heart-related diseases and colonic hypersensitivity associated with psychopathological disturbance and stress.

13 Claims, No Drawings

1H-IMIDAZO[4,5-D]PYRIDAZIN-7-ONE, AND CORRESPONDING THIONES AS CORTICOTROPIN RELEASING FACTOR (CRF) RECEPTOR LIGANDS

This application is a division of U.S. Ser. No. 09/473,870, filed Dec. 28, 1999, now U.S. Pat. No. 6,271,380 which is a continuation of U.S. Provisional Application Ser. No. 60/114,188, filed Dec. 30, 1998.

FIELD OF THE INVENTION

This invention relates a treatment of psychiatric disorders and neurological diseases including major depression, anxiety-related disorders, post-traumatic stress disorder, supranuclear palsy and feeding disorders as well as treatment of immunological, cardiovascular or heart-related diseases and colonic hypersensitivity associated with psychopathological disturbance and stress, by administration of certain 1H-imidazo[4,5-d]pyridazin-7-ones, 3H-imidazo-[4,5-c]pyridin-4-ones and corresponding thiones.

BACKGROUND OF THE INVENTION

Corticotropin releasing factor (herein referred to as CRF), a 41 amino acid peptide, is the primary physiological regulator of proopiomelanocortin (POMC)-derived peptide secretion from the anterior pituitary gland [J. Rivier et al., *Proc. Nat. Acad. Sci. (USA)* 80:4851 (1983); W. Vale et al., *Science* 213:1394 (1981)]. In addition to its endocrine role at the pituitary gland, immunohistochemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in brain [W. Vale et al., *Rec. Prog. Horm. Res.* 39:245 (1983); G. F. Koob, *Persp. Behav. Med.* 2:39 (1985); E. B. De Souza et al., *J. Neurosci.* 5:3189 (1985)]. There is also evidence that CRF plays a significant role in integrating the response of the immune system to physiological, psychological, and immunological stressors [J. E. Blalock, *Physiological Reviews* 69:1 (1989); J. E. Morley, *Life Sci.* 41:527 (1987)].

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system [for review see E. B. De Souza, *Hosp. Practice* 23:59 (1988)].

In affective disorder, or major depression, the concentration of CRF is significantly increased in the cerebral spinal fluid (CSF) of drug-free individuals [C. B. Nemeroff et al., *Science* 226:1342 (1984); C. M. Banki et al., *Am. J. Psychiatry* 144:873 (1987); R. D. France et al., *Biol. Psychiatry* 28:86 (1988); M. Arato et al., *Biol Psychiatry* 25:355 (1989)]. Furthermore, the density of CRF receptors is significantly decreased in the frontal cortex of suicide victims, consistent with a hypersecretion of CRF [C. B. Nemeroff et al., *Arch. Gen. Psychiatry* 45:577 (1988)]. In addition, there is a blunted adrenocorticotropin (ACTH) response to CRF (i.v. administered) observed in depressed patients [P. W. Gold et al., *Am J. Psychiatry* 141:619 (1984); F. Holsboer et al., *Psychoneuroendocrinology* 9:147 (1984); P. W. Gold et al., *New Eng. J. Med.* 314:1129 (1986)]. Preclinical studies in rats and non-human primates provide additional support for the hypothesis that hypersecretion of CRF may be involved in the symptoms seen in human depression [R. M. Sapolsky, *Arch. Gen. Psychiatry* 46:1047 (1989)]. There is preliminary evidence that tricyclic antidepressants can alter CRF levels and thus modulate the numbers of CRF receptors in brain [Grigoriadis et al., *Neuropsychopharmacology* 2:53 (1989)].

There has also been a role postulated for CRF in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., *Life Sci.* 31:363 (1982); C. W. Berridge and A. J. Dunn *Regul. Peptides* 16:83 (1986)]. Preliminary studies using the putative CRF-receptor antagonist a-helical ovine CRF (9-41) in a variety of behavioral paradigms demonstrate that the antagonist produces ìanxiolytic-likeîeffects that are qualitatively similar to the benzodiazepines [C. W. Berridge and A. J. Dunn *Horm. Behav.* 21:393 (1987), *Brain Research Reviews* 15:71 (1990)]. Neurochemical, endocrine and receptor binding studies have all demonstrated interactions between CRF and benzodiazepine anxiolytics providing further evidence for the involvement of CRF in these disorders. Chlordiazepoxide attenuates the ìanxiogenicî effects of CRF in both the conflict test [K. T. Britton et al., *Psychopharmacology* 86:170 (1985); K. T. Britton et al., *Psychopharmacology* 94:306 (1988)] and in the acoustic startle test [N. R. Swerdlow et al., *Psychopharmacology* 88:147 (1986)] in rats. The benzodiazepine receptor antagonist (Ro15-1788), which was without behavioral activity alone in the operant conflict test, reversed the effects of CRF in a dose-dependent manner while the benzodiazepine inverse agonist (FG7142) enhanced the actions of CRF [K. T. Britton et al., *Psychopharmacology* 94:306 (1988)].

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist ($\alpha$-helical $CRF_{9-41}$) in a variety of behavioral paradigms have demonstrated that the CRF antagonist produces ìanxiolytic-likeî effects qualitatively similar to the benzodiazepines [for review see G. F. Koob and K. T. Britton, In: *Corticotropin-Releasing Factor: Basic and Clinical Studies of a Neuropeptide*, E. B. De Souza and C. B. Nemeroff eds., CRC Press p221 (1990)].

Several publications describe corticotropin releasing factor antagonist compounds and their use to treat psychiatric disorders and neurological diseases. Examples of such publications include DuPont Merck PCT application US94/11050, Pfizer WO 95/33750, Pfizer WO 95/34563, Pfizer WO 95/33727 and Pfizer EP 0778 277 A1.

SUMMARY OF THE INVENTION

In accordance with one aspect, the present invention provides novel compounds, pharmaceutical compositions and methods which may be used in the treatment of affective disorder, anxiety, depression, irritable bowel syndrome, post-traumatic stress disorder, supranuclear palsy, immune suppression, Alzheimer's disease, gastrointestinal disease, anorexia nervosa or other feeding disorder, drug or alcohol withdrawal symptoms, drug addiction, inflammatory disorder, fertility problems, disorders, the treatment of which can be effected or facilitated by antagonizing CRF, including but not limited to disorders induced or facilitated by CRF, or a disorder selected from inflammatory disorders such as rheumatoid arthritis and osteoarthritis, pain, asthma, psoriasis and allergies; generalized anxiety disorder; panic, phobias, obsessive-compulsive disorder; post-traumatic stress disorder; sleep disorders induced by stress; pain perception such as fibromyalgia; mood disorders such as depression, including major depression, single episode depression, recurrent depression, child abuse induced depression, and postpartum depression; dysthemia; bipolar disorders; cyclothymia; fatigue syndrome; stress-induced headache; cancer, human immunodeficiency virus (HIV) infections; neurodegenerative diseases such as Alzheimer's disease, Parkinson's disease and Huntington's disease; gastrointestinal diseases such as ulcers, irritable bowel syndrome, Crohn's disease, spastic colon, diarrhea, and post operative ilius and colonic hypersensitivity associated by psychopathological disturbances or stress; eating disorders such as anorexia and bulimia nervosa; hemorrhagic stress; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; cardiovascular and hear related disorders including hypertension, tachycardia and congestive heart failure; stroke; immune dysfunctions including stress induced immune dysfunctions (e.g., stress induced fevers, porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g, dependencies on alcohol, cocaine, heroin, benzodiazepines, or other drugs); drug and alcohol withdrawal symptoms; osteoporosis; psychosocial dwarfism and hypoglycemia in a mammal.

The present invention provides novel compounds which bind to corticotropin releasing factor receptors, thereby altering the anxiogenic effects of CRF secretion. The compounds of the present invention are useful for the treatment of psychiatric disorders and neurological diseases, anxiety-related disorders, post-traumatic stress disorder, supranuclear palsy and feeding disorders as well as treatment of immunological, cardiovascular or heart-related diseases and colonic hypersensitivity associated with psychopathological disturbance and stress in a mammal.

According to another aspect, the present invention provides novel compounds of Formula (1) (described below) which are useful as antagonists of the corticotropin releasing factor. The compounds of the present invention exhibit activity as corticotropin releasing factor antagonists and appear to suppress CRF hypersecretion. The present invention also includes pharmaceutical compositions containing such compounds of Formula (1) and methods of using such compounds for the suppression of CRF hypersecretion, and/or for the treatment of anxiogenic disorders.

According to yet another aspect of the invention, the compounds provided by this invention (and especially labelled compounds of this invention) are also useful as standards and reagents in determining the ability of a potential pharmaceutical to bind to the CRF receptor.

DETAILED DESCRIPTION OF INVENTION

[1] The present invention comprises novel compounds of Formula (1) (described below) which are useful as antagonists of the corticotropin releasing factor. The compounds of the present invention exhibit activity as corticotropin releasing factor antagonists and appear to suppress CRF hypersecretion. This invention comprises compounds of Formula (1):

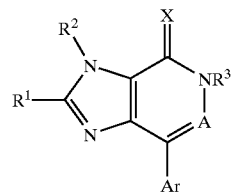

and isomers thereof, stereoisomeric forms thereof, or mixtures of stereoisomeric forms thereof, and pharmaceutically acceptable salt or pro-drug forms thereof, wherein:

X is O or S;

A=N or $CR^9$;

Ar is selected from phenyl, naphthyl, pyridyl, pyrimidinyl, triazinyl, furanyl, thienyl, benzothienyl, benzofuranyl, 2,3-dihydrobenzofuranyl, 2,3-dihydrobenzothienyl, indanyl, 1,2-benzopyranyl, 3,4-dihydro-1,2-benzopyranyl, tetralinyl, each Ar optionally substituted with 1 to 5 $R^4$ groups and each Ar is attached via an unsaturated carbon atom;

$R^1$ is independently selected at each occurrence from H, $C_1$–$C_4$†alkyl, $C_2$–$C_4$†alkenyl, $C_2$–$C_4$†alkynyl, halo, CN, $C_1$–$C_4$†haloalkyl, $C_1$–$C_{12}$ hydroxyalkyl, $C_2$–$C_{12}$ alkoxyalkyl, $C_2$–$C_{10}$ cyanoalkyl, $C_3$–$C_6$ cycloalkyl, $C_4$–$C_{10}$ cycloalkylalkyl, $NR^9R^{10}$, $C_1$–$C_4$ alkyl-$NR^9R^{10}$, $NR^9COR^{10}$, $OR^{11}$, SH or $S(O)_nR^{12}$;

$R^2$ is selected from:
—H, aryl, heteroaryl and heterocyclyl, or
—$C_1$–$C_{10}$†alkyl, $C_2$–$C_{10}$†alkenyl, $C_2$–$C_{10}$†alkynyl, $C_3$–$C_8$†cycloalkyl, $C_5$–$C_8$ cycloalkenyl, $C_4$–$C_{12}$†cycloalkylalkyl or $C_6$–$C_{10}$ cycloalkenylalkyl, each optionally substituted with 1 to 3 substituents independently selected at each occurrence from $C_1$–$C_6$†alkyl, $C_3$–$C_6$†cycloalkyl, $C_{1-6}$ alkyloxy$C_{1-6}$ alkyl, $C_{2-6}$ alkenyl, $C_{3-6}$ alkynyl, halo, $C_1$–$C_4$†haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl and heterocyclyl;

$R^3$ is selected from:
—H, aryl, heteroaryl and heterocyclyl, or
$C_1$–$C_4$†lkyl, $C_3$–$C_6$†alkenyl, $C_3$–$C_6$†alkynyl, $C_3$–$C_6$†cycloalkyl, $C_4$–$C_{10}$ cycloalkylalkyl, each optionally substituted with 1 to 3 substituents independently selected at each occurrence from $C_1$–$C_6$†alkyl, $C_3$–$C_6$†cycloalkyl, halo, $C_1$–$C_4$†haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl and heterocyclyl;

$R^4$ is independently selected at each occurrence from: $C_1$–$C_{10}$†alkyl, $C_2$–$C_{10}$†alkenyl, $C_2$–$C_{10}$†alkynyl, $C_3$–$C_6$ cycloalkyl, $C_4$–$C_{12}$†cycloalkylalkyl, $NO_2$, halo, CN, $C_1$–$C_4$†haloalkyl, $NR^6R^7$, $NR^6COR^7$, $NR^6CO_2R^7$, $COR^7$, $OR^7$, $CONR^6R^7$, $CO(NOR^9)R^7$, $CO_2R^7$, or $S(O)_nR^7$, where each such $C_1$–$C_{10}$†alkyl, $C_2$–$C_{10}$†alkenyl, $C_2$–$C_{10}$†alkynyl, $C_3$–$C_6$ cycloalkyl and $C_4$–$C_{12}$†cycloalkylalkyl are optionally substituted with 1 to 3 substituents independently selected at each occurrence from $C_1$–$C_4$ alkyl, $NO_2$, halo, CN, $NR^6R^7$, $NR^6COR^7$, $NR^6CO_2R^7$, $COR^7$ $OR^7$, $CONR^6R^7$, $CO_2R^7$, $CO(NOR^9)R^7$, or $S(O)_nR^7$;

$R^6$ and $R^7$ are independently selected at each occurrence from:
- —H,
- —$C_1$–$C_{10}$ alkyl, $C_3$–$C_{10}$ alkenyl, $C_3$–$C_{10}$ alkynyl, $C_1$–$C_{10}$ haloalkyl with 1–10 halogens, $C_2$–$C_8$ alkoxyalkyl, $C_3$–$C_6$†cycloalkyl, $C_4$–$C_{12}$†cycloalkylalkyl, $C_5$–$C_{10}$ cycloalkenyl, or $C_6$–$C_{14}$ cycloalkenylalkyl, each optionally substituted with 1 to 3 substituents independently selected at each occurrence from $C_1$–$C_6$†alkyl, $C_3$–$C_6$†cycloalkyl, halo, $C_1$–$C_4$†aloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl,
- -aryl, aryl($C_1$–$C_4$ alkyl), heteroaryl, heteroaryl($C_1$–$C_4$ alkyl), heterocyclyl or heterocyclyl($C_1$–$C_4$ alkyl);

alternatively, $NR^6R^7$ is piperidine, pyrrolidine, piperazine, N-methylpiperazine, morpholine or thiomorpholine, each optionally substituted with 1–3 $C_1$–$C_4$ alkyl groups;

$R^8$ is independently selected at each occurrence from H or $C_1$–$C_4$ alkyl optionally substituted by halogen, $C_1$–$C_4$ alkoxy or $C_1$–$C_4$ halo-alkoxy (1 to 4 halogens);

$R^9$ and $R^{10}$ are independently selected at each occurrence from H, $C_1$–$C_4$ alkyl, or $C_3$–$C_6$ cycloalkyl;

$R^{11}$ is selected from H, $C_1$–$C_4$ alkyl, $C_1$–$C_4$ haloalkyl, or $C_3$–$C_6$ cycloalkyl;

$R^{12}$ is $C_1$–$C_4$ alkyl or $C_1$–$C_4$ haloalkyl;

$R^{13}$ is selected from $C_1$–$C_4$ alkyl, $C_1$–$C_4$ haloalkyl, $C_2$–$C_8$ alkoxyalkyl, $C_3$–$C_6$†cycloalkyl, $C_4$–$C_{12}$†cycloalkylalkyl, aryl, aryl($C_1$–$C_4$ alkyl)—, heteroaryl or heteroaryl($C_1$–$C_4$ alkyl)—;

$R^{15}$ and $R^{16}$ are independently selected at each occurrence from H, $C_1$–$C_6$ alkyl, $C_3$–$C_{10}$ cycloalkyl, $C_4$–$C_{16}$ cycloalkylalkyl, except that for $S(O)_nR^{15}$, $R^{15}$ cannot be H;

aryl is phenyl or naphthyl, each optionally substituted with 1 to 5 substituents independently selected at each occurrence from $C_1$–$C_6$†alkyl, $C_3$–$C_6$†cycloalkyl, halo, $C_1$–$C_4$†haloalkyl, cyano, $OR^{15}$, SH, $S(O)_nR^{15}$, $COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$, $NR^{16}R^{15}$, and $CONR^{16}R^{15}$;

heteroaryl is pyridyl, pyrimidinyl, triazinyl, furanyl, pyranyl, quinolinyl, isoquinolinyl, thienyl, imidazolyl, thiazolyl, indolyl, pyrrolyl, oxazolyl, benzofuranyl, benzothienyl, benzothiazolyl, isoxazolyl, pyrazolyl, 2,3-dihydrobenzothienyl or 2,3-dihydrobenzofuranyl, each being optionally substituted with 1 to 5 substituents independently selected at each occurrence from $C_1$–$C_6$†alkyl, $C_3$–$C_6$†cycloalkyl, halo, $C_1$–$C_4$†haloalkyl, cyano, $OR^{15}$, SH, $S(O)_nR^{15}$, —$COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$, $NR^{16}R^{15}$, and $CONR^{16}R^{15}$;

heterocyclyl is saturated or partially saturated heteroaryl, optionally substituted with 1 to 5 substituents independently selected at each occurrence from $C_1$–$C_6$†alkyl, $C_3$–$C_6$†cycloalkyl, halo, $C_1$–$C_4$†haloalkyl, cyano, $OR^{15}$, SH, $S(O)_nR^{15}$, $COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$, $NR^{15}R^{16}$, and $CONR^{16}R^{15}$;

n is independently at each occurrence 0, 1 or 2.

[2] Preferred compounds of the above invention also include compounds of Formula (1) and isomers thereof, stereoisomeric forms thereof, or mixtures of stereoisomeric forms thereof, and pharmaceutically acceptable salt or pro-drug forms thereof wherein Ar is phenyl or pyridyl, each optionally substituted with 1 to 4 $R^4$ substituents.

[3] More preferred compounds of the above invention also include compounds and isomers thereof of formula 1 wherein A is equal to nitrogen (formula 1a), stereoisomeric forms thereof, or mixtures of stereoisomeric forms thereof, and pharmaceutically acceptable salt or pro-drug forms thereof.

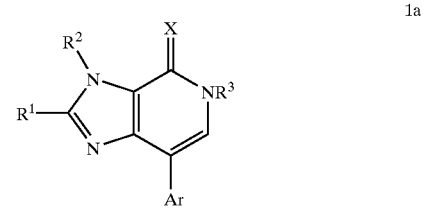

1a

[4] The present invention also relates to compounds, compositions, and stereoisomeric forms, pharmaceutical salts or pro-drugs thereof wherein, in a compound of formula 1, A is equal to $CR^9$ (formula 1b):

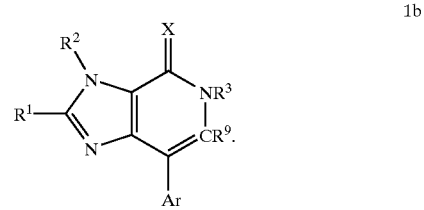

1b

[5] More preferred compounds of the invention include those compounds of formula 1 wherein X is equal to oxygen.

[6] More preferred compounds of the above invention also include compounds and isomers thereof, stereoisomeric forms thereof, or mixtures of stereoisomeric forms thereof, and pharmaceutically acceptable salt or pro-drug forms thereof wherein Ar is phenyl or pyridyl and each Ar is optionally substituted with 1 to 3 $R^4$ substituents.

[7] More preferred compounds of the above invention also include compounds and isomers thereof, stereoisomeric forms thereof, or mixtures of stereoisomeric forms thereof, and pharmaceutically acceptable salt or pro-drug forms thereof wherein $R^2$ is:

$C_1$–$C_{10}$†alkyl, $C_2$–$C_{10}$†alkenyl, $C_2$–$C_{10}$†alkynyl, $C_3$–$C_8$†cycloalkyl, $C_5$–$C_8$ cycloalkenyl, $C_4$–$C_{12}$†cycloalkylalkyl or $C_6$–$C_{10}$ cycloalkenylalkyl, each optionally substituted with 1 to 3 substituents independently selected at each occurrence from $C_1$–$C_6$†alkyl, $C_3$–$C_6$†cycloalkyl, halo, $C_1$–$C_4$†haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl and heterocyclyl.

[8] More preferred compounds also include those compounds of formula 1 wherein $R^1$, $R^2$ and $R^3$ are independently selected at each position from $zC_{1-6}$ alkyl.

[9] The present invention comprises a method of treating affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated by antagonizing CRF, including but not limited to disorders induced or facilitated by CRF, in mammals comprising administering to the mammal a therapeutically effective amount of a compound of Formula (1) with the variables as recited above.

The present invention also provides pharmaceutical compositions comprising compounds of Formula (1) with the variables as recited above and a pharmaceutically acceptable carrier.

Many compounds of this invention have one or more asymmetric centers or planes. Unless otherwise indicated, all chiral (enantiomeric and diastereomeric) and racemic forms are included in the present invention. Many geometric isomers of olefins, C=N double bonds, and the like can also be present in the compounds, and all such stable isomers are contemplated in the present invention. The compounds may be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

The term "alkyl" includes both branched and straight-chain alkyl having the specified number of carbon atoms. Commonly used abbreviations have the following meanings: Me is methyl, Et is ethyl, Pr is propyl, Bu is butyl. The prefix "n" means a straight chain alkyl. The prefix "c" means a cycloalkyl. The prefix "(S)" means the S enantiomer and the prefix "(R)" means the R enantiomer. Alkenyl" includes hydrocarbon chains of either a straight or branched configuration and one or more unsaturated carbon-carbon bonds which may occur in any stable point along the chain, such as ethenyl, propenyl, and the like. "Alkynyl" includes hydrocarbon chains of either a straight or branched configuration and one or more triple carbon-carbon bonds which may occur in any stable point along the chain, such as ethynyl, propynyl and the like. "Haloalkyl" is intended to include both branched and straight-chain alkyl having the specified number of carbon atoms, substituted with 1 or more halogen; "alkoxy" represents an alkyl group of indicated number of carbon atoms attached through an oxygen bridge; "cycloalkyl" is intended to include saturated ring groups, including mono-,bi- or poly-cyclic ring systems, such as cyclopropyl, cyclobutyl, cyclopentyl, cyclohexyl, and so forth. "Halo" or "halogen" includes fluoro, chloro, bromo, and iodo.

The term "substituted", as used herein, means that one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "appropriate amino acid protecting group" means any group known in the art of organic synthesis for the protection of amine or carboxylic acid groups. Such amine protecting groups include those listed in Greene and Wuts, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference. Any amine protecting group known in the art can be used. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl.

The term "pharmaceutically acceptable salts" includes acid or base salts of the compounds of Formulae (1) and (2). Examples of pharmaceutically acceptable salts include, but are not limited to, mineral or organic acid salts of basic residues such as amines; alkali or organic salts of acidic residues such as carboxylic acids; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Prodrugs" are considered to be any covalently bonded carriers which release the active parent drug of formula (I) or (II) in vivo when such prodrug is administered to a mammalian subject. Prodrugs of the compounds of formula (I) and (II) are prepared by modifying functional groups present in the compounds in such a way that the modifications are cleaved, either in routine manipulation or in vivo, to the parent compounds. Prodrugs include compounds wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups in the compounds of formulas (I) and (II); and the like.

The term "therapeutically effective amount" of a compound of this invention means an amount effective to antagonize abnormal level of CRF or treat the symptoms of affective disorder, anxiety or depression in a host.

Syntheses

Some compounds of Formula (1) where X=O and A=N, may be prepared from intermediate compounds of Formula (3) using the procedures outlined in Scheme 1. Compounds of Formula (3) may be treated with a halogenating agent in the presence or absence of a base in the presence or absence of an inert solvent at reaction temperatures ranging from −80° C. to 250° C. to give products of Formula (4) (where X is halogen). Halogenating agents include, but are not limited to, $Br_2$, $Cl_2$, $I_2$, N-bromosuccinimide, N-iodosuccinimide or N-chlorosuccinimide. Bases may include, but are not limited to, alkali metal carbonates, alkali metal bicarbonates, trialkyl amines (preferably N,N-di-isopropyl-N-ethyl amine) or aromatic amines (preferably pyridine). Inert solvents may include, but are not limited to, lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane). Preferred reaction temperatures range from −20° C. to 150° C. The resulting intermediates (4) may then be reacted with alcohols $R^2OH$, where $R^2$ is defined above, in the presence of phosphines $R^a{}_3P$ (where $R^a$ is lower alkyl, phenyl or substituted phenyl or furyl) and an azodicarboxylate ester $R^bO_2CN=NCO_2R^b$ (where $R^b$ is lower alkyl)in an inert solvent at temperatures ranging from −80° C. to 150° C. Inert solvents may include, but are not limited to, polyethers (preferably 1,2-dimethoxyethane), dialkyl ethers (preferably diethyl ether), cyclic ethers (preferably tetrahydrofuran or 1,4-dioxane) or aromatic hydrocarbons (preferably benzene or toluene). The choices of phosphine, solvent or azodicarboxylate ester are known to those skilled in the art as described by O. Mitsunobu (Synthesis, 1 [1981]). Intermediates (5) are treated with a base or an alkali metal in an inert solvent and then reacted with formylating agents YCHO. Y is a halogen, alkoxy, dialkylamino, alkylthio, alkanoyloxy, alkanesulfonyloxy or cyano group. Bases may include, but are not limited to, alkyl lithiums, alkali metal hydrides (preferably sodium hydride), alkaline earth metal halides (e.g. methylmagnesium bromide), alkaline earth metal hydrides, alkali metal dialkylamides (preferably lithium di-isopropylamide) and alkali metal bis(trialkylsilyl)-amides (preferably sodium bis(trimethylsilyl)amide). Inert solvents include, but are not limited to, dialkyl ethers (preferably diethyl ether), cyclic ethers (preferably tetrahydrofuran or 1,4-dioxane), or aromatic hydrocarbons (preferably benzene or toluene). Preferred reaction temperatures range from −80° C. to 100° C.

Scheme 1

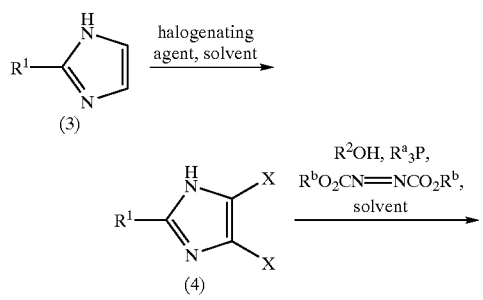

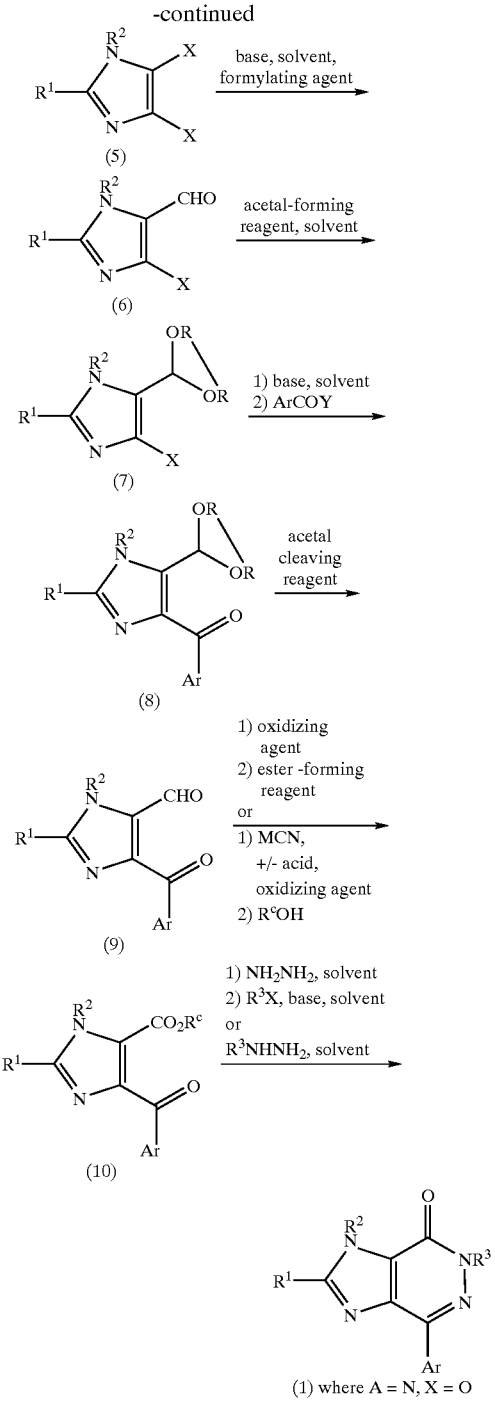

The resulting aldehydes (6) may be converted to acetals (7) by treatment with an acetal-forming reagent in the presence or absence of an acid in an inert solvent. The dotted line between the R groups means that they may or may not be connected. Acetal-forming reagents may be alcohols ROH, where R is lower alkyl, diols HOR—ROH where R—R is lower alkylene, or orthoesters $HC(OR)_3$ where R is lower alkyl. Inert solvents may include, but are not limited to, water, alkyl alcohols (1 to 8 carbons, preferably methanol or ethanol), lower alkanenitriles (1 to 6 carbons, preferably acetonitrile), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide) or aromatic hydrocarbons (preferably benzene or toluene). Acids may include, but are not limited to alkanoic acids of 2 to 10 carbons (preferably acetic acid), haloalkanoic acids (2–10 carbons, 1–10 halogens, such as trifluoroacetic acid), arylsulfonic acids (preferably p-toluenesulfonic acid or benzenesulfonic acid), alkanesulfonic acids of 1 to 10 carbons (preferably methanesulfonic acid), hydrochloric acid, sulfuric acid or phosphoric acid. Stoichiometric or catalytic amounts of such acids may be used. Preferred temperatures range from ambient temperature to 150° C.

Acetals (7) may then be reacted with a base in an inert solvent, followed by treatment with a compound ArCOY (where Y is a halogen, alkoxy, dialkylamino, alkylthio, alkanoyloxy, alkanesulfonyloxy or cyano group) to afford intermediates (8). Bases may include, but are not limited to, alkyl lithiums, alkali metal dialkylamides (preferably lithium di-isopropylamide) or alkali metal bis(trialkylsilyl) amides (preferably sodium bis(trimethylsilyl)amide. Inert solvents may include, but are not limited to, dialkyl ethers (preferably diethyl ether), cyclic ethers (preferably tetrahydrofuran or 1,4-dioxane or aromatic hydrocarbons (preferably benzene or toluene). Intermediates (8) may then be converted to compounds of Formula (9) by treatment with an acetal-cleaving reagent in an inert solvent. Acetal-cleaving reagents may include, but are not limited to, hydrochloric acid, sulfuric acid, phosphoric acid, alkanoic acids, alkylsulfonic acids, substituted phenylsulfonic acids, camphorsulfonic acid or haloalkylsulfonic acids. Inert solvents may include, but are not limited to, water, alkyl alcohols (1 to 8 carbons, preferably methanol or ethanol), lower alkanenitriles (1 to 6 carbons, preferably acetonitrile), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide) or aromatic hydrocarbons (preferably benzene or toluene).

The keto-aldehydes (9) may be converted to esters (10) by treatment with an oxidizing agent in an inert solvent to give a carboxylic acid, followed by treatment with an ester-forming reagent. Oxidizing agents include transition metal oxides, such as $CrO_3$ or $KMnO_4$ (with or without a buffering agent such as $NaH_2PO_4$), pyridinium dichromate or pyridine-$SO_3$ complex. Inert solvents include water, alkanones (e.g. acetone), aqueous solutions of HCl or $H_2SO_4$, or N,N-dialkylformamides. Ester-forming reagents include but are not limited to alcohols $R^cOH$, where $R^c$ is lower alkyl, or orthoesters $HC(OR^c)_3$ or combinations of a halogenating reagent and an alcohol $R^cOH$ used sequentially or in the same reaction. Halogenating agents include, but are not limited to, $POCl_3$, $(COCl)_2$, $SOCl_2$, N-halosuccinimides, $PCl_3$, $PCl_5$ or PBr3. Inert solvents for the halogenation include, but are not limited to, aromatic hydrocarbons (preferably benzene or toluene), aromatic amines (e.g. pyridine) or haloalkanes of 1 to 10 carbons and 1 to 10 halogens (preferably dichloromethane). Preferred reaction temperatures range from 0° C. to 150° C.

Alternatively, aldehydes (9) may be reacted with a compound MCN, where M is H, alkali metal or tetraalkylammonium moiety, in an inert solvent, treated with an oxidizing agent and reacted with alcohols $R^cOH$ where $R^c$ is lower alkyl. Oxidizing include, but are not limited to, transition metal oxides, such as $CrO_3$ or $MnO_2$, pyridine-chromium complexes, such as $CrO_3.C_5H_5N$, pyridinium dichromate or pyridinium chlorochromate or an oxalylchloride-dimethylsulfoxide-triethylamine reagent system, commonly called the Swern oxidation system (D. Swern et al., J. Organic. Chem., 43, 2480–2482 (1978)). Inert solvents of the oxidation include, but are not limited to, halocarbons of 1 to 6 carbons, preferably dichloromethane or 1,2-dichloroethane, lower alkyl alcohols, preferably ethanol or methanol, or lower alkanoic acids, dialkyl ethers (preferably diethyl ether), cyclic ethers (preferably tetrahydrofuran or 1,4-dioxane), or combinations thereof.

Esters (10) may then be converted to compounds of Formula (1) where X=O and A=N by one of two methods. Esters (10) may be reacted with hydrazine or its hydrate in an inert solvent, then treated with an alkylating agent in the presence or absence of a base in an inert solvent to provide compounds of Formula (1) where X is O and A=N. Phase transfer catalysts (e.g. tetra-alkylammonium halides or hydroxides) may be optionally employed for the alkylations. Alternatively, esters (10) may be reacted with compounds of Formula $R^3NHNH_2$ (where $R^3$ is defined above) in the presence or absence of a base in an inert solvent. Alkylating agents are compounds of the formula $R^3Z$, where Z is halogen, alkanesulfonyloxy (e.g. mesylate), substituted phenylsulfonyloxy (e.g. tosylate) or haloalkanesulfonyloxy (e.g. triflate) groups. Bases may include, but are not limited to, alkali metal carbonates, alkali metal bicarbonates, alkyl lithiums, alkali metal hydrides (preferably sodium hydride), alkali metal alkoxides (1 to 6 carbons) (preferably sodium methoxide or sodium ethoxide), alkaline earth metal hydrides, alkali metal dialkylamides (preferably lithium di-isopropylamide), alkali metal hydroxides, alkali metal bis(trialkylsilyl)amides (preferably sodium bis(trimethylsilyl)amide), trialkyl amines (preferably N,N-di-isopropyl-N-ethyl amine or triethylamine) or aromatic amines (preferably pyridine). Inert solvents may include, but are not limited to, water, lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene), haloalkanes of 1 to 10 carbons and 1 to 10 halogens (preferably dichloromethane) or combinations thereof. Preferred reaction temperatures range from −80° C. to 100° C.

Compounds of Formula (1) where A=N and X=O may be converted to compounds of Formula (1) where A=N and X=S according to the procedures outlined in Scheme 2. Compounds of Formula (1) where A=N, X=O and $R^3$=H may be converted to compounds of Formula (1) where A=N, X=S and $R^3$=H by treatment with a thiocarbonyl-forming reagent in an inert solvent. Thiocarbonyl-forming reagents include but are not limited to, $P_2S_5$ or Lawessonís reagent. Inert solvents may include, but are not limited to, lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane). Preferred reaction temperatures range from 0° C. to 160° C. These intermediates may then be converted to compounds of Formula (1) where A=N, X=S and $R^3$ is not equal to H by treatment with an alkylating agent in the presence or absence of a base in an inert solvent. Alkylating agents are compounds of the formula $R^3Z$, where Z is halogen, alkanesulfonyloxy (e.g. mesylate), substituted phenylsulfonyloxy (e.g. tosylate) or haloalkanesulfonyloxy (e.g. triflate) groups. Bases may include, but are not limited to, alkali metal carbonates, alkali metal bicarbonates, alkyl lithiums, alkali metal hydrides (preferably sodium hydride), alkali metal alkoxides (1 to 6 carbons) (preferably sodium methoxide or sodium ethoxide), alkaline earth metal hydrides, alkali metal dialkylamides (preferably lithium di-isopropylamide), alkali metal bis(trialkylsilyl)amides (preferably sodium bis(trimethylsilyl)amide), trialkyl amines (preferably N,N-di-isopropyl-N-ethyl amine or triethylamine) or aromatic amines (preferably pyridine). Inert solvents may include, but are not limited to, lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane). Preferred reaction temperatures range from −80° C. to 150° C. Alternatively, Compounds of Formula (1) where A=N, X=O and $R^3$ is not equal to H may be converted to compounds of Formula (1) where A=N, X=S and $R^3$ is not equal to H by treatment with a thiocarbonyl-forming reagent in an inert solvent. The reagent and inert solvent are defined above.

metal hydrides (preferably sodium hydride), alkali metal alkoxides (1 to 6 carbons) (preferably sodium methoxide or sodium ethoxide), alkaline earth metal hydrides, alkali metal dialkylamides (preferably lithium di-isopropylamide), alkali metal bis(trialkylsilyl)amides (preferably sodium bis(trimethylsilyl)amide). Inert solvents include, but are not limited to, dialkyl ethers (preferably diethyl ether) or cyclic ethers (preferably tetrahydrofuran or 1,4-dioxane). Intermediates (12) may be hydrolyzed to give intermediates (13) in the presence of an acid in an inert solvent. Acids may include, but are not limited to alkanoic acids of 2 to 10 carbons (preferably acetic acid), haloalkanoic acids (2–10 carbons, 1–10 halogens, such as trifluoroacetic acid), arylsulfonic acids (preferably p-toluenesulfonic acid or benzenesulfonic acid), alkanesulfonic acids of 1 to 10 carbons (preferably methanesulfonic acid), hydrochloric acid, sulfuric acid or phosphoric acid. Stoichiometric or catalytic amounts of such acids may be used. Preferred temperatures range from ambient temperature to 150° C. Aldehydes (13) may be treated with amines $R^3NH_2$ to generate compounds of Formula (1) where A=$CR^8$ in the presence or absence of an acid or base in an inert solvent. Acids may include, but are not limited to alkanoic acids of 2 to 10 carbons (preferably acetic acid), haloalkanoic acids (2–10 carbons, 1–10 halogens, such as trifluoroacetic acid), arylsulfonic acids (preferably p-toluenesulfonic acid or benzenesulfonic acid), alkanesulfonic acids of 1 to 10 carbons (preferably methanesulfonic acid), hydrochloric acid, sulfuric acid or phosphoric acid. Stoichiometric or catalytic amounts of such acids may be used. Bases may include, but are not limited to, alkali metal carbonates, alkali metal bicarbonates, alkyl lithiums, alkali metal hydrides (preferably sodium hydride), alkali metal alkoxides (1 to 6 carbons) (preferably sodium methoxide or sodium ethoxide), alkaline earth metal hydrides, alkali metal dialkylamides (preferably lithium di-isopropylamide), alkali metal bis(trialkylsilyl)amides (preferably sodium bis(trimethylsilyl)amide). Inert solvents may include, but are not limited to, water, alkyl alcohols (1 to 8 carbons, preferably methanol or ethanol), lower alkanenitriles (1 to 6 carbons, preferably acetonitrile), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide) or aromatic hydrocarbons (preferably benzene or toluene). Preferred temperatures range from ambient temperature to 150° C.

Scheme 2

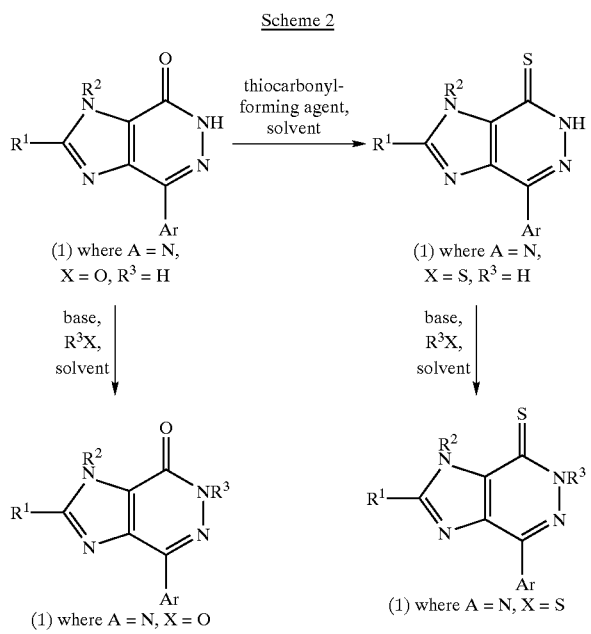

Scheme 3

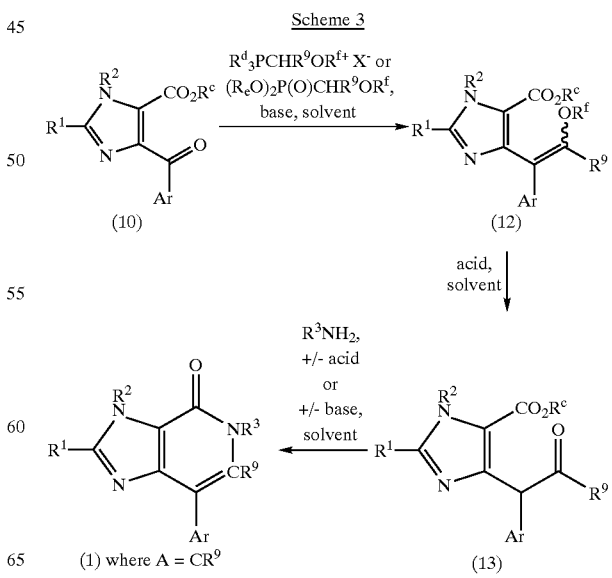

Compounds of Formula (1) where A=$CR^9$ may be prepared from esters (10) by the methods outlined in Scheme 3. Esters (10) may be treated with phosphonium salts of the formula $R^d{}_3PCH\,R^9OR^{f+}X^-$ where $R^d$ is phenyl or substituted phenyl or phosphonates $(R^eO)_2P(O)CHR^9OR^f$ in the presence of a base in an inert solvent to give enol ethers (12). Bases may include, but are not limited to, alkali metal carbonates, alkali metal bicarbonates, alkyl lithiums, alkali

Scheme 4

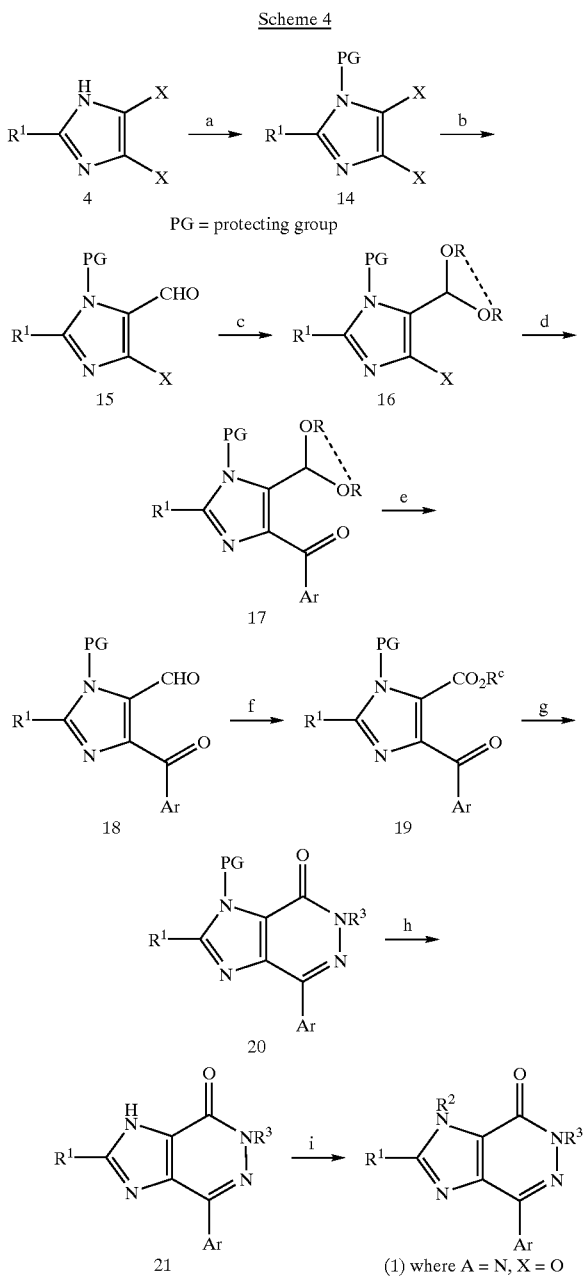

PG = protecting group

Reagents: (a) PG-X/ base/solvent, (b) base, solvent, formylating agent, (c) acetal-forming reagent, (d) base, solvent, ArCOY, (e) acetal cleaving reagent, (f) 1. oxidizing agent, 2. ester-forming reagent or MCN, +/- acid, R$^c$OH, (g) 1. NH$_2$NH$_2$, solvent, 2. R$_3$X, base, solvent or R$_3$NHNH$_2$, solvent, (h) deprotecting agents, (i) mitsunobu reactio or R$_2$X, base, solvent Alternatively, imidazo[4,5-d]pyridazin-7-ones may be obtained from intermediate (4) as shown in Scheme 4. The intermediate (4) may converted to compound of formula (14) using protecting groups but not limited to benzyl, p-MeO-benzyl or benzyloxymethyl groups. Compound 14 may be converted to compound 20 using the conditions previously described for Scheme 1. Compound 10 may then be deprotected to its NH derivative (21) by standard conditions known in literature. Compound 21 may alkylated under mitsunobu conditions described in Scheme 1 or by alkylation using a base and alkyl halides in the presence of a solvent.

EXAMPLES

Analytical data were recorded for the compounds described below using the following general procedures. Proton NMR spectra were recorded on an Varian FT-NMR (300 MHz); chemical shifts were recorded in ppm (δ) from an internal tetramethysilane standard in deuterochloroform or deuterodimethylsulfoxide as specified below. Mass spectra (MS) or high resolution mass spectra (HRMS) were recorded on a Finnegan MAT 8230 spectrometer (using chemi-ionization (CI) with NH$_3$ as the carrier gas or gas chromatography (GC) as specified below) or a Hewlett Packard 5988A model spectrometer. Melting points were recorded on a Buchi Model 510 melting point apparatus and are uncorrected. Boiling points are uncorrected. All pH determinations during workup were made with indicator paper.

Reagents were purchased from commercial sources and, where necessary, purified prior to use according to the general procedures outlined by D. Perrin and W. L. F. Armarego, *Purification of Laboratory Chemicals*, 3rd ed., (New York: Pergamon Press, 1988). Chromatography (thin layer (TLC) or preparative) was performed on silica gel using the solvent systems indicated below. For mixed solvent systems, the volume ratios are given. Otherwise, parts and percentages are by weight.

The following examples are provided to describe the invention in further detail. These examples, which set forth the best mode presently contemplated for carrying out the invention, are intended to illustrate and not to limit the invention.

Example 1

4-(2,4-dichlorophenyl)-2-ethyl-1-(1-ethyl)propyl-imidazo[4,5-d]pyridazin-7-one

Part A: 4,5-dibromo-2-ethyl-1H-imidazole
Method A

A solution of 2-ethylimidazole (57.6 g, 0.6 moles) in CHCl$_3$ (700 mL) was cooled to 0–5° C. and then bromine was added (76.8 mL, 1.5 moles) dropwise over 60 min under nitrogen atmosphere. The mixture was stirred at 5° C. for 60 mins and then at room temperature for 2 days. TLC (1:10 MeOH/CH$_2$Cl$_2$) revealed disappearance of starting material (Rf=0.25) and showed a new spot (Rf=0.45). The mixture was cooled back to 0° C. and a 2N aq. NaOH solution (750 mL) added dropwise to dissolve the yellow solid separated from the mixture. The aqueous layer was separated and extracted the organic layer with 250 mL of 2N NaOH. The combined aqueous extracts was acidified to pH 8.0 using a concentrated HCl solution. The cream-colored solid separated and it was filtered, washed with water and dried in vacuo at 50° C. to afford 55.0 g of desired product (mp 149–150° C., 36% yield): $^1$H NMR (CDCl$_3$): δ1.27–1.3 (t, 3H, CH$_3$), 2.7–2.8 (q, 2H, CH$_2$). Mass spectrum (CI-NH$_3$) m/z: 255.0 (M+H).

Method B

To a solution of imidazole (2.32 g, 0.0242 moles) in DMF (30.0 mL) was added KHCO$_3$ (6.1 g, 0.061 moles) and then added bromine (3.12 mL, 0.061 moles) dropwise over 30 mins. at room temp. The mixture was then stirred at 70° C. for 4 hours and then cooled to room temp. TLC (1:10 MeOH/CH$_2$Cl$_2$) revealed a new spot (Rf=0.45) along with disappearance of starting material (Rf=0.25). The inorganic materials were filtered, washed the inorganic solids with ethyl acetate and concentrated the filtrate in vacuo to an oil. The oil was treated with water (50.0 mL) and the resulting solid was filtered and dried to afford 4.59 g of a solid ((mp, 149–150° C., 75% yield).

Part B: 4,5-dibromo-2-ethyl-1-(1-ethyl)propyl-1H-imidazole

A mixture of part A material (8.3 g, 0.033 moles), triphenylphosphine (9.4 g, 0.036 moles) and molecular sieves (10 g) in THF (100 mL) was cooled to 0 to −5° C. and then 3-pentanol (3.4 g, 0.039 moles) was added under nitrogen atmosphere. The mixture was stirred at 0° C. for 30 mins and then diisopropylazodicarboxylate (7.2 g, 0.033 moles) was added dropwise over 20 min. The mixture was stirred at 0° C. for 2 hours followed by room temperature for 2 days and TLC (1:50 MeOH/CH$_2$Cl$_2$) revealed a new spot at Rf=0.5. The reaction mixture was filtered, the collected solid was washed with dichloromethane and the solvent was removed in vacuo to afford yellow liquid. The crude was purified by flash column chromatography using chloroform as eluent to afford 4.9 g (46.5%) of colorless oil. $^1$H NMR (CDCl$_3$): δ0.79–0.84 (t, 6H, 2*CH$_3$), 1.3–1.35 (t, 3H, CH$_3$), 1.82–2.18 (m, 4H, 2*CH$_2$), 2.65–2.72 (q, 2H, CH$_2$), 3.95 (m, 1H, CH). Mass spectrum (CINH$_3$): m/z 325.0 (M+H).

Part C: 4-bromo-2-ethyl-1-(1-ethyl)propyl-1H-imidazole-5-carboxaldehyde

A solution of Part B material (3.7 g, 0.0114 moles) in THF (40.0 mL) was cooled to −78° C. under nitrogen atmosphere and then a 1.6 M n-BuLi solution in hexane (7.4 mL, 0.0119 moles) added dropwise over 30 mins. The mixture was stirred at −78° C. for 1 h and then DMF (2.7 mL, 0.0342 moles) was added dropwise over 15 min. The mixture was stirred at −78° C. for 60 min and quenched with saturated NH$_4$Cl (10 mL) at −78° C. TLC (1:50 MeOH/CH$_2$Cl$_2$) revealed a new spot at Rf=0.55 along with disappearance of starting material spot at Rf=0.5. The reaction mixture was extracted with diethyl ether (3*25 mL), washed with brine and dried (MgSO$_4$). The solvent was removed in vacuo to afford a yellow oil which was purified by flash column chromatography on silica gel using chloroform as eluent to afford 1.97 g (64% yield) of colorless oil. $^1$H NMR (CDCl$_3$): δ0.73–0.83 (t, 6H, 2*CH$_3$), 1.35–1.40 (t, 3H, CH$_3$), 1.59–2.17 (m, 4H, 2*CH$_2$), 2.72–2.80 (q, 2H, CH$_2$), 3.95 (m, 1H, CH), 9.67 (s, 1H, CHO). Mass spectrum (CI-NH$_3$): m/z 275.1 (M+2H).

Part D: 4-bromo-2-ethyl-1-(1-ethyl)propyl-1H-imidazole-5-carboxaldehyde ethylene glycol acetal A mixture of part C material (1.75 g, 0.0064 moles) in benzene (150 mL) was treated with ethylene glycol (1.2 mL, 0.025 moles), pyridine (0.0035 moles) and p-toluenesulfonic acid mono hydrate (0.0035 moles). The reaction mixture was heated at reflux in a 20 mL capacity Dean-Stark trap equipped apparatus for 24 hours and TLC (1:50 MeOH/CH$_2$Cl$_2$) revealed a new spot at Rf=0.35 (visible under iodine). The reaction mixture was cooled to room temperature, diluted with EtOAc (50 mL), washed with 10% sodium bicarbonate, brine and dried (MgSO$_4$). The solvent was evaporated under reduced pressure to furnish yellow oil. The crude was purified by flash column chromatography on silica gel using 25% ethyl acetate/chloroform mixture to afford 1.96 g (97%) white solid (mp 70–71° C.). $^1$H NMR (CDCl$_3$): δ0.78–0.89 (t, 6H, 2*CH$_3$), 1.29–1.36 (t, 3H, CH$_3$), 1.77–1.90 (m, 4H, 2*CH$_2$), 2.70–2.73 (q, 2H, CH$_2$), 3.98–4.3 (m, 5H, CH and 2*CH$_2$), 5.86 (s, 1H, CH). Mass spectrum (CI-NH$_3$): 317.1 (M$^+$). Anal. calcd. for C$_{13}$H$_{22}$Br$_1$N$_2$O$_2$: C, 49.22; H, 6.67; N, 8.83. Found: C, 49.43; H, 6.61; N, 8.78.

Part E: 4-(2,4-dichlorobenzoyl)-2-ethyl-1-(1-ethyl)propyl-1H-imidazole-5-carboxaldehyde A solution of part D material (1.08 g, 0.0034 moles) in THF (20.0 mL) was cooled to −78° C. and then a 1.6 M n-BuLi in hexane (2.4 mL, 0.004 moles) was added dropwise over 15 min under nitrogen atmosphere. The mixture was stirred at −78° C. for 2.5 h and then a solution of 2,4-dichlorobenzoyl chloride (0.84 g, 0.004 moles) in THF (5.0 mL) was added over 15 mins. The mixture was stirred at −78° C. for 6 h followed by room temperature overnight and TLC (30:70 EtOAc/hexane) showed a new spot at Rf=0.43. The mixture was quenched with saturated NH$_4$Cl (10.0 ml), extracted with ethyl acetate (3*30 mL), washed with brine and dried (MgSO$_4$). The solvent was stripped off in vacuo to afford crude product which was purified by flash column chromatography on a silica gel using 15% EtOAC/hexane to afford 0.61 g (44% yield) of desired product as yellow oil. Mass spectrum (CI-NH$_3$): 411.2 (M$^+$). The acetal was dissolved in acetone (15.0 mL) and treated with a 3.0 M aqueous HCl solution (30.0 mL) at room temperature. The reaction mixture was stirred for 24 h at this temperature and TLC (30:70 EtOAc/hexane) showed a new spot at Rf=0.55. It was then quenched with saturated NaCl (50.0 ml), extracted with ethyl acetate (3*50 mL), washed with brine and dried (MgSO$_4$). The solvent was removed in vacuum to afford yellow liquid and purified the crude by flash column chromatography on a silica gel using 15% EtOAC/hexane to afford 0.28 g (51% yield) of desired product as yellow solid (mp 85–86° C.). $^1$H NMR (CDCl$_3$): δ0.785 (m, 6H, 2*CH$_3$), 1.28–1.33 (t, 3H, CH$_3$), 1.90–2.23 (m, 4H, 2*CH$_2$), 2.74–2.82 (q, 2H, CH$_2$), 3.98–4.05 (m, 1H, CH), 7.34–7.37 (d, 1H, aromatic), 7.45–7.46 (d, 1H, aromatic), 7.55–7.58 (d, 1H, aromatic). Mass spectrum (CI-NH$_3$): 367 (M$^+$). Anal. calcd. for C$_{18}$H$_{20}$Cl$_2$N$_2$O$_2$: C, 58.87; H, 5.50; N, 7.64. Found: C, 58.91; H, 5.60; N, 7.44.

Part F: Methyl 4-(2,4-dichlorobenzoyl)-2-ethyl-1-(1-ethyl)propyl-imidazo-5-carboxylate A mixture of Part E material (0.367 g, 0.001 moles) in methanol (60 mL) was reacted with NaCN (Aldrich, 0.245 g, 0.005 moles, 5 equiv.), AcOH (Baker, 96 mg; 0.0016 moles, 1.6 equiv.) and MnO$_2$, activated (Aldrich, 1.24 g, 0.021 moles, 21 equiv.). The resulting mixture was stirred at room temp under nitrogen for 18 h. TLC (1:50 MeOH/CH$_2$Cl$_2$) revealed absence of starting material spot at Rf=0.8 and showed a new spot at Rf=0.44. The reaction mixture was filtered through celite, washed with methanol, concentrated in vacuo and the crude was purified by flash column chromatography on a silica gel using 1:100 MeOH/CH$_2$Cl$_2$ as eluent to afford 320 mg (mp 73–74° C., 81%) of white solid after crystallization from hexane. Anal. calcd. for C$_{19}$H$_{22}$Cl$_2$N$_2$O$_3$: C,57.44; H,5.58; N, 7.05. Found: C,57.31; H,5.45; N,6.85.

Part G: Title Compound

A mixture of Part F material (0.100 g, 0.00025 moles) in ethanol (10 mL) was treated with anhydrous hydrazine (0.105 g, 0.0033 moles) and refluxed under nitrogen for 48 h. TLC (30:70 EtOAc/hexane) showed a new spot at Rf=0.35. The solvent was removed under vacuum and purified the crude by flash column chromatography on a silica gel using 15:85 EtOAc/hexane initially and then methanol to afford 70 mg (74% yield) of the product as white solid after tituration of the oil with diethyl ether (mp 246–247° C.). HRMS calcd. for C$_{18}$H$_{21}$Cl$_2$N$_4$O$_1$: 379.1092. Found: 379.1070 (M+H).

Example 2

4-(2,4-dichlorophenyl)-2-ethyl-1-(1-ethyl)propyl-6-(N-methyl)imidazo[4,5-d]pyridazin-7-one A mixture of Part F material of example 1 (0.100 g, 0.00025 moles) in ethanol (10 mL) was treated with anhydrous methylhydrazine (0.150 g, 0.0033 moles) and refluxed under nitrogen for 8 days. TLC (1:50 MeOH/CH$_2$Cl$_2$) showed a new spot at Rf=0.55. The solvent was removed under vacuum and purified the crude by flash column chromatography on a silica gel 1:50 MeOH/CH$_2$Cl$_2$ to afford 30 mg (31% yield) of the product as white solid (mp 94–95° C.). HRMS calcd. for C$_{19}$H$_{23}$Cl$_2$N$_4$O$_1$: 393.1249. Found: 393.1250 (M+H).

Example 3

4-(2,4-dichlorophnyl)-2-ethyl-6-(N-ethyl)-1-(1-ethyl)propyl-imidazo[4,5-d]pyridazin-7-one To a solution of Part G of example 1 (0.1 g, 0.264 mmoles) in benzene (5.0 mL) was added n-tetrabutylammonium bromide (8.5 mg, 0.0264 mmoles), powdered KOH (15.0 mg, 0.264 mmoles) and iodoethane (0.124 g, 0.79 mmoles). The resultant mixture was stirred at room temperature under nitrogen for 20 h. TLC (1:50 MeOH/CH$_2$Cl$_2$) showed a new spot at Rf=0.73 along with disappearance of starting material (Rf=0.33). The reaction mixture was diluted with EtOAc (10 mL), washed with brine (10 mL), dried with MgSO$_4$ and concentrated to a residue. The crude was purified by flash column chromatography on a silica gel using dichloromethane as eluent to afford 58 mg (54% yield) of the product as colorless oil. HRMS calcd. for C$_{20}$H$_{25}$N$_4$Cl$_2$O$_1$: 407.1405. Found: 407.1404 (M+H).

Example 4

4-(2,4-dichlorophenyl)-2-ethyl-1-(1-ethyl)propyl-6-(N-propyl)-imidazo[4,5-d]pyridazin-7-one The title compound was prepared using Part G of example 1 material and 1-iodopropane and following the conditions outlined in example 3 to afford desired product as colorless oil (56 mg, 51% yield). Anal. calcd. for C$_{21}$H$_{26}$N$_4$Cl$_2$O$_1$: C, 59.86; H, 6.23; N, 13.30. Found: C,59.86; H,6.12; N, 13.13.

Example 5

6-(N-cyclopropylmethyl)-4-(2,4-dichlorophenyl)-2-ethyl-1-(1-ethyl)propyl-imidazo[4,5-d]pyridazin-7-one The title compound was prepared using Part G of example 1 material and bromomethylcyclopropane and following the conditions outlined in example 3 to afford desired product as colorless oil (68 mg, 59% yield). HRMS calcd. for C$_{22}$H$_{27}$N$_4$Cl$_2$O$_1$:433.1562. Found: 433.1563 (M+H).

Example 6

4-Bis(2,4-trifluoromethylphenyl)-2-ethyl-1-(1-ethyl) propyl-6-(N-methyl)-imidazo[4,5-d]pyridazin-7-one
Part A: A solution of part D material of example
1 in THF (30.0 mL) was cooled to −78° C. and then added dropwise 1.6 M n-BuLi in hexane over 15 mins. The mixture was stirred at −78° C. for 2½ h and then added a solution of 2,4-(CF$_3$)$_2$—Ph—COCl in 5.0 mL of THF over 15 mins. The mixture was stirred at −78° C. for 6 h and then warm to room temp and stirred overnight. The reaction mixture was quenched with a saturated NH$_4$Cl solution (50.0 ml), extracted with ethyl acetate (3*30 mL), the combined organic extracts were washed with brine and the solvent was removed under vacuum to afford an orange yellow liquid (4.3 g). TLC (30:70 EtOAc/hexane) of the crude showed absence of starting material spot (Rf=0.4) along with a new spot at Rf=0.47. The crude was purified by flash column chromatography on a silica gel using 30% EtOAC/hexane to afford 1.53 g (mp 105–106° C., 64% yield) of desired benzoyl derivative as white solid. Mass spec. (CI-NH$_3$): 479.2 (M+H). Anal. calcd. for C$_{22}$H$_{24}$N$_2$O$_3$F$_6$: C, 55.23; H, 5.07; N, 5.87. Found; C, 54.96; H, 5.09; N, 5.72.

Part B: A solution of part A material of example 6 (1.43 g, 2.9 mmoles) in acetone (30.0 mL) was cooled to 15° C. and then added 3M aq. HCl (60.0 mL) over 15 mins. The mixture was stirred below 30° C. for 24 h. TLC (30:70 EtOAc/hexane) showed a new spot at Rf=0.63 along with disappearance of starting material (Rf=0.43). The solvent was removed under vacuum, extracted with ethyl acetate (3*50 mL), washed with brine and stripped off the solvent in vacuum to afford yellow liquid. The crude was purified by flash column chromatography on a silica gel using dichloromethane as eluent to afford 1.03 g (82% yield) of desired aldehyde as yellow liquid. Mass spec. (NH$_3$-CI): 435 (M+H). Anal. calcd. for C$_{20}$H$_{20}$N$_2$O$_2$F$_6$: C, 55.30; H, 4.64; N,6.46. Found; C,55.03; H,4.45; N,6.27.

Part C: A mixture of part B material of example 6 (0.434 g, 1.0 mmole) in methanol (30 mL) was treated with NaCN (Aldrich, 0.245 g, 5.0 mmoles, 5 equiv.), AcOH (Baker, 96 mg; 1.6 mmoles, 1.6 equiv.) and MnO$_2$, activated (Aldrich, 1.24 g, 21.0 mmoles, 21 equiv.). The resulting mixture was stirred at room temp under nitrogen for 24 h. TLC (30:70 EtOAc/hexane) revealed absence of starting material at Rf=0.63 and showed a new spot at Rf=0.55. The reaction mixture was filtered through celite, washed with methanol, concentrated in vacuo. The residue was diluted with water, extracted with ethyl acetate, washed with brine, dried and concentrated in vacuo to afford yellow oil. The crude was purified by flash column chromatography on a silica gel using 30:70 EtOAc/hexane as eluent to afford 350 mg (mp 57–58° C., 75%) of pale yellow solid. Mass spec. (NH$_3$-CI) 465.3 (M+H). Anal. calcd. for C$_{21}$H$_{22}$N$_2$O$_3$F$_6$: C, 54.31; H, 4.79; N, 6.03. Found: C,53.92; H,4.68; N, 5.80.

Part D: Title Compound: A mixture of Part C material of example 6 (0.116 g, 0.250 mmoles) in ethylene glycol (3.0 mL) was treated with anhydrous methylhydrazine (0.15 g, Aldrich, 3.3 mmoles, 13 equiv.) and refluxed under nitrogen for 20 h. TLC (30:70 EtOAc/hexane) revealed both starting material and product had identical Rf values (0.55). The reaction mixture was cooled to room temperature and poured over 25 mL of water, extracted with EtOAc (3*15 mL), washed with brine and dried. The solvent was removed under vacuo and purified the crude by flash column chromatography on a silica gel using 30% EtOAc/hexane to afford an oil which was crystallized from hexane to afford 16 mg (14% yield; mp 139–140° C.) of white solid as desired product. HRMS calcd. for C$_{21}$H$_{23}$N$_4$O$_1$F$_6$: 461.1776. Found: 461.1763 (M+H).

Example 7

(±)-4-(2,4-dichlorophenyl)-2-ethyl-6-(N-methyl)-1-(1-methyl)butyl-imidazo[4,5-d]pyridazin-7-one Part A: To a solution of 4,5-dibromo-2-ethyl-1-(2-pentyl)-1H-imidazole (37.5 g, 0.116 moles, prepared according to the method described in Part B of example 1) in THF (250 mL) was cooled to −78° C. and then a 1.6 M n-BuLi in hexane added dropwise (76.0 mL, 0.122 moles) over 45 mins. The mixture was stirred at −78° C. for 1 h (brown solution) and then added DMF (27.0 g, 0.348 moles) dropwise over 30 mins. The mixture was stirred at −78° C. for 60 mins. The reaction mixture was quenched with saturated ammonium chloride (100 mL) at −78° C. and brought to room temperature. The reaction mixture was extracted with ethyl ether (3*100 mL), washed with brine and dried with anhydrous $MgSO_4$. The solvent was evaporated under reduced pressure to afford 31.6 g of crude yellow oil. The crude was purified by flash column chromatography on a silica gel using chloroform as eluent to afford 18.5 g (59% yield) of desired aldehyde as colorless oil. Anal. calcd. for $C_{11}H_{17}N_2OBr$; C, 48.36; H, 6.27; N, 10.25. Found: C,48.64; H,6.01; N,10.00.

Part B: A mixture of part A material of example 7 (18.5 g, 0.068 moles) in benzene (250 mL) was treated with ethylene glycol (16.4 g, 0.264 moles), pyridine (2.7 g, 0.034 moles) and p-toluenesulfonic acid monohydrate (6.5 g, 0.034 moles). The reaction mixture was heated at reflux in a 20 mL capacity Dean-Stark trap equipped apparatus for 36 h. TLC (30:70 EtOAc/hexane) revealed a new spot at Rf=0.42 (visible under iodine) along with disappearance of starting material (Rf=0.54). The reaction mixture was cooled to room temperature, diluted with EtOAc (250 mL), washed with 10% sodium bicarbonate (2*250 mL), brine and dried ($MgSO_4$). The solvent was evaporated under reduced pressure to furnish acetal as white solid (20.7 g, mp 69–70° C., 96%). Mass spectrum (CI-$NH_3$): 317.1 ($M^+$). Anal. calcd. for $C_{13}H_{22}N_2O_2Br_1$; C,49.22; H, 6.67, N, 8.83. Found: C,49.38; H,6.62; N, 8.68.

Part C: A solution of Part B material of example 7 (2.73 g, 0.01 moles) in THF (30 mL) was cooled to −78° C. and then added dropwise 1.6 M n-BuLi in hexane (7.4 mL) over 15 mins. The mixture was stirred at −78° C. for 2½ h and then added a solution of 2,4-dichlorobenzoyl chloride in 5.0 mL of THF over 15 mins. The mixture was stirred at −78° C. for 6 h and then warm to room temp and stirred overnight. The reaction mixture was quenched with satd. $NH_4Cl$ (50.0 ml), extracted with ethyl acetate (3*30 mL), washed with brine and stripped off the solvent in vacuum to afford orange yellow liquid (4.3 g). TLC (30:70 EtOAc/hexane) of the crude showed absence of starting material spot (Rf=0.4) and a new spot at Rf=0.47. The crude was purified by flash column chromatography on a silica gel using 30% EtOAC/hexane to afford 2.4 g (mp 129–130° C., 59% yield) of benzoyl derivative as white solid. Mass spec. (CI-NH3): 411 ($M^+$). Anal. calcd. for $C_{20}H_{24}N_2O_3Cl_2$: C, 58.40; H, 5.88; N, 6.81. Found: C, 58.45; H, 5.95; N, 6.68.

Part D: A solution of part C material of example 7 (2.3 g, 0.056 moles) in acetone (60 mL) was cooled to 15° C. and then added 3M aq. HCl (120 mL) over 15 mins. The mixture was stirred below 30° C. for 24 h. TLC (30:70 EtOAc/hexane) showed a new spot at Rf=0.58 along with disappearance of starting material (Rf=0.43). The solvent was removed under vacuum, extracted with ethyl acetate (3*50 mL), washed with brine and stripped off the solvent in vacuum to afford yellow liquid (2.4 g). The crude was purified by flash column chromatography on a silica gel using dichloromethane as eluent to afford 1.46 g (71% yield) of keto aldehyde derivative as yellow solid (mp 43–44° C.). Mass spec. ($NH_3$-CI): 367 ($M^+$). Anal. calcd. for $C_{18}H_{20}N_2O_2Cl_2$: C, 58.87; H, 5.50; N,7.64. Found: C,58.96; H,5.34; N,7.46.

Part E: A mixture of Part D material of example 7(1.0 g, 0.0027 moles) in methanol (50 mL) was treated with NaCN (Aldrich, 0.67 g, 0.0136 moles, 5 equiv.), AcOH (Baker, 260 mg; 0.00432 moles, 1.6 equiv.) and $MnO_2$, activated (Aldrich, 3.34 g, 0.057 moles, 21 equiv.). The resulting mixture was stirred at room temp under nitrogen for 20 h. TLC (30:70 EtOAc/hexane) revealed absence of starting material at Rf=0.58 and showed a new spot at Rf=0.4. The reaction mixture was filtered through celite, washed with methanol, concentrated in vacuo. The residue was diluted with water, extracted with ethyl acetate, washed with brine, dried and concentrated in vacuo to afford 0.98 g of yellow oil. The crude was purified by flash column chromatography on a silica gel using 30:70 EtOAc/hexane as eluent to afford 910 mg (85%) of keto ester derivative as yellow oil. Mass spec.: 397.2 ($M^+$). Anal. calcd. for $C_{19}H_{22}N_2O_3Cl_2$: C,57.44; H,5.58; N,7.05. Found: C, 57.25; H, 5.70; N, 6.80.

Part F: Title Compound: A mixture of Part E material of example 7 (0.100 g, 0.00025 moles) in ethylene glycol (2 mL) was treated with anhydrous methylhydrazine (0.105 g, 0.0033 moles) and refluxed under nitrogen for 4 h. TLC (30:70 EtOAc/hexane) revealed a new spot (Rf=0.44) along with disappearance of starting material (Rf=0.4. The reaction mixture was cooled to room temp and poured over 25 mL of water, extracted with EtOAc (3*15 mL), washed with brine and dried. The solvent was removed under vacuo and purified the crude by flash column chromatography on a silica gel using 15% EtOAc/hexane to afford colorless oil which was crystallized from hexane to afford 42 mg of white solid (43%, mp 89–90° C.). Mass spec. (CI-$NH_3$): 393.2 ($M^+$). Anal. calcd. for $C_{19}H_{22}N_4Cl_2O$: C, 58.02; H, 5.65; N, 14.24. Found: C,58.32; H, 5.59; N, 14.14.

Example 8

(±)-4-(2,4-dichlorophenyl)-2-ethyl-1-(1-methyl) butyl-imidazo[4,5-d]pyridazin-7-one A mixture of Part E material of example 7 (0.460 g, 0.00115 moles) in ethylene glycol (5 mL) was treated with anhydrous hydrazine (0.48 g, 0.0151 moles) and refluxed under nitrogen for 4 h. TLC (30:70 EtOAc/hexane) revealed a new spot (Rf=0.44) along with disappearance of starting material (Rf=0.4). The reaction mixture was cooled to room temp and poured over 25 mL of water, extracted with EtOAc (3*15 mL), washed with brine and dried. The solvent was removed under vacuo and purified the crude by flash-column chromatography on a silica gel using 15% EtOAc/hexane to afford colorless oil which was crystallized from hexane to afford 310 mg of white solid (71%, mp 217–18° C.). Mass spec. (CI-$NH_3$):379.2 ($M^+$). Anal. calcd. for $C_{18}H_{20}N_4Cl_2O$: C, 57.00; H,5.33; N,14.77. Found: C,57.02; H, 5.35; N, 14.59.

Example 9

(±)-4-(2,5-dimethyl-4-methoxyphenyl)-2-ethyl-6-(N-methyl)-1-(1-methyl)butyl-imidazo[4,5-d]pyridazin-7-one Part A: Synthesis of 2,5-dimethyl-4-methoxybenzoyl chloride: To a stirred mixture of 2,5-dimethyl-4-methoxybenzaldehyde (6.7 g, 0.004 moles) in acetone (140 mL) at 60° C. was added $KMnO_4$ (8.46 g, 0.0054 moles) dissolved in water (250 mL) dropwise over 30 mins. The reaction mixture quickly turned into brown suspended solution. The reaction mixture was further continued for 1 h. The reaction mixture was cooled to room temp., filtered through celite and extracted with diethyl ether. The aq. layer was acidified with con. HCl, filtered the white solid separated, washed with water and dried at 50° C. for 30 mins under vacuum to afford 3.46 g of carboxylic acid as white solid (mp 161–162° C., 48% yield). The carboxylic acid (3.4 g, 0.0189 moles) was dissolved in 75 mL of anhydrous benzene and added few drops of pyridine followed by addition of thionyl chloride (5.0 mL, 0.0689, 3.65 equiv., fw 118.97, d 1.631). The resultant mixture was refluxed at reflux for 20 h. The solvent was removed under vacuum, the solid thus resulted was treated with 5.0 mL of hexane and filtered the undissolved white solid (3.7 g, mp 84–85° C., 98.7%).

Part B: A solution of part B material of example 7 (2.73 g, 0.01 moles) in THF was cooled to −78° C. and then added dropwise 1.6 M n-BuLi in hexane (7.4 mL, 0.0115 moles) over 15 mins. The mixture was stirred at −78° C. for 2½ h and then added a solution of 2,5-(Me)$_2$-4-OMe—Ph—COCl (2.2 g, 0.012 moles) in 10.0 mL of THF over 15 mins. The mixture was stirred at −78° C. for 6 h and then warm to room temp and stirred overnight. The reaction mixture was quenched with satd. NH$_4$Cl (50.0 ml), extracted with ethyl acetate (3*30 mL), washed with brine and stripped off the solvent in vacuum to afford orange yellow liquid. TLC (30:70 EtOAc/hexane) of the crude showed absence of starting material spot (Rf=0.4) along with product spot appeared at Rf=0.38. The crude was purified by flash column chromatography on a silica gel using 15% EtOAC/hexane to afford 1.53 g (mp 160–162° C., 38% yield) of desired benzoyl derivative as pale yellow solid. Mass spec. (CI-NH$_3$): 401.3 (M+H). Anal. calcd. for C$_{23}$H$_{32}$N$_2$O$_4$: C, 68.97; H, 8.05; N, 6.99. Found; C, 69.05; H, 8.10; N, 6.33.

Part C: A solution of part B material of example 9 (1.4 g, 0.0035 moles) in acetone (30 mL) was cooled to 15° C. and then added 3M aq. HCl (60 mL) over 15 mins. The mixture was stirred below 30° C. for 24 h. TLC (30:70 EtOAc/hexane) showed product spot at 0.56. The solvent was removed under vacuum, extracted with ethyl acetate (3*50 mL), washed with brine and stripped off the solvent in vacuum to afford yellow liquid. The crude was purified by flash column chromatography on a silica gel using dichloromethane, followed by 1% MeOH/dichloromethane as eluents to afford 0.48 g (39% yield) of desired product as yellow liquid. HRMS calcd. for C$_{21}$H$_{29}$N$_2$O$_3$:357.2178. Found:357.2169 (M+H)

Part D: A mixture of part C material of example 9 (0.357 g, 1.0 mmole) in methanol (30 mL) was treated with NaCN (Aldrich, 0.245 g, 5.0 Mmoles, 5 equiv.), AcOH (Baker, 96 mg; 1.6 mmoles, 1.6 equiv.) and MnO$_2$, activated (Aldrich, 1.24 g, 21.0 mmoles, 21 equiv.). The resulting mixture was stirred at room temp under nitrogen for 24 h. TLC (30:70 EtOAc/hexane) revealed absence of starting material at Rf=0.56 and showed a new spot at Rf=0.30. The reaction mixture was filtered through celite, washed with methanol, concentrated in vacuo. The residue was diluted with water, extracted with ethyl acetate, washed with brine, dried and concentrated in vacuo to afford yellow oil. The crude was purified by flash column chromatography on a silica gel using 30:70 EtOAc/hexane as eluent to afford 205 mg (53%) of ketoester derivative as pale yellow oil. HRMS calcd. for C$_{22}$H$_{30}$N$_2$O$_4$: 386.2205. Found: 387.2264 (M+H).

Part E: A mixture of part D material of example 9 (0.100 g, 0.000259 moles) in ethylene glycol (3.0 mL) was treated with anhydrous methylhydrazine (0.15 g, Aldrich, 0.0033 moles, 13 equiv.) and refluxed under nitrogen for 14 h. TLC (30:70 EtOAc/hexane) revealed a new spot (Rf=0.40) along with disappearance of starting material (Rf=0.3). The reaction mixture was cooled to room temp and poured over 25 mL of water, extracted with EtOAc (3*15 mL), washed with brine and dried. The solvent was removed under vacuo and purified the crude by flash column chromatography on a silica gel using 30% EtOAc/hexane to afford 43 mg (43% yield) of a solid: HRMS calcd. for C$_{22}$H$_{31}$N$_4$O$_2$: 383.2447. Found: 383.2433 (M+H).

Using the above procedures and modifications known to one skilled in the art of organic synthesis, the following additional examples of Tables 1–4 may be prepared.

The examples delineated in Tables 1, 2, 3 and 4 may be prepared by the methods outlined in Examples 1, 2 or 3 or combinations thereof. Commonly used abbreviations are: Ph is phenyl, Pr is propyl, Me is methyl, Et is ethyl, Bu is butyl, Ex is Example, amorph. is amorphous.

Example 544

4-(2,4-Dichlorophenyl)-2-ethyl-6-(N-methyl)-imidazo[4,5-d]pyridazin-7-one

Part A: Synthesis of 1-[(Benzyloxy)methyl]4,5-dibromo-2-ethylimidazole: To a mechanically stirred solution of 4,5-dibromo-2-ethylimidazole (25.4 g, 0.1 mole,) in anhydrous DMF (250 mL) was treated with K$_2$CO$_3$ (69.1 g, fw=138.2, 0.5 moles, 5 equiv.) followed by dropwise addition of benzyl chloromethyl ether (18.5 g, 0.11 moles, 93% pure, TCI, fw=156.61) and stirred overnight at room temp under nitrogen for 20 h. TLC (30:70 EtOAc/hexane) revealed absence of starting material imidazole (Rf=0.2) along with formation of product (Rf=0.71). The reaction mixture was filtered, washed the solid with dichloromethane and the combined filterate was evaporated under reduced pressure and purified the crude (47 g) by flash column chromatography (dichloromethane eluent) to afford 31.75 g (85%) of colorless oil. Mass spectrum (m/z=375, M+H).

Part B: Synthesis of 1-[(Benzyloxy)methyl]-4-bromo-2-ethyl-5-formylimidazole: A solution of 1-[(Benzyloxy)methyl]-4,5-dibromo-2-ethylimidazole (28.0 g, 75.0 mmol, Part A of example 544) in THF (300 mL) was cooled to −78° C. under nitrogen atmosphere and then added dropwise 1.6 M n-BuLi in hexane (51.75 mL, 82.5 mmol, Aldrich) over 30 mins. The mixture was stirred at −78° C. for 30 mins and then added DMF (16.5 g, 225 mmol, Aldrich) dropwise over 15 mins. The mixture was stirred at −78° C. for 30 mins. A small portion of the reaction mixture was quenched with satd. NH$_4$Cl at −78° C. TLC (30:70 EtOAc/hexane) revealed both starting material and product showed almost identical Rf values (0.71 & 0.70) along with another minor spot at Rf=0.15. However, mass spectrum (CI-NH$_3$) revealed absence of starting material and formation of product (m/z=325, M+2H). The reaction mixture was quenched with satd. ammonium chloride (20 mL) at −78° C. and brought to room temp. The reaction mixture was extracted with ethyl acetate (3×100 mL), washed with brine and dried with anhydrous MgSO$_4$. The solvent was evaporated under reduced pressure to afford crude yellow oil. The crude was purified by flah column chromatography on a silica gel using dichloromethane as eluent to afford 22.6 g (93%) of colorless oil. HRMS calcd. for C$_{14}$H$_{16}$N$_2$O$_2$Br: 323.0395. Found:323.0394 (M+H).

Part C: 1-[(Benzyloxy)methyl]-4-bromo-2-ethyl-5-formylimidazole ethylene acetal: A mixture of 1-[(Benzyloxy)methyl]-4-bromo-2-ethyl-5-formyl-imidazole (22.6 g, 0.0699 moles) in benzene (400 mL) was treated with ethylene glycol (16.9 g, 0.273 moles, fw 62, 3.9 equiv.), pyridine (2.76 g, 0.03495 moles, fw=79.1, 0.5 equiv.) and p-toluenesulfonic acid monohydrate (6.6 g, 0.03495 moles, fw=190, 0.5 equiv). The reaction mixture was heated at reflux in a 20 mL capacity Dean-Stark trap equipped apparatus for 24 hours. TLC (30:70 EtOAc/hexane) revealed a new spot at Rf=0.35 (visible under iodine) along with disappearance of starting material (Rf=0.70). The reaction mixture was cooled to room temperature, diluted with EtOAc (100 mL), washed with 10% sodium bicarbonate, brine and dried (MgSO$_4$). The solvent was evaporated under reduced pressure to furnish yellow oil. The crude was purified by flash column chromatography on silica gel using 25% ethyl acetate/hexane mixture to afford 22.8 g (89%) colorless oil. $^1$H NMR (CDCl$_3$): 1.29–1.33 (t, 3H, CH$_3$), 2.71–2.78 (q, 2H, CH$_2$), 3.96 (s, 4H, 2×OCH$_2$), 4.55 (s, 2H, CH$_2$), 5.4 (S, 2H, CH$_2$), 5.88 (S, 1H, CH), 7.27–7.38 (M, 5H, aromatic). HRMS calcd. for C$_{16}$H$_{20}$N$_2$O$_3$Br$_1$: 367.0658. Found: 367.0653 (M+H).

Part D: 1-[(Benzyloxy)methyl]-4-(2,4-dichlorobenzoyl)-2-ethyl-5-formylimidazole ethylene acetal: A solution of 1-[(Benzyloxy)methyl]-4-bromo-2-ethyl-5-formyl-imidazole ethylene acetal (22.5 g, 0.0613 moles, fw=367.25, Part C of Example 544) in THF (200.0 mL) was cooled to −78° C. and then added dropwise 1.6 M n-BuLi in hexane (43.7 mL, 0.071 moles, 1.1 equiv.) over 15 mins under nitrogen atmosphere. The mixture was stirred at −78° C. for 90 mins and then added a solution of 2,4-dichlorobenzoyl chloride (14.3 g, 0.071 moles, 1.1 equiv.) in THF (5.0 mL) over 15 mins. The mixture was stirred at −78° C. for 4 h followed by room temperature overnight. TLC (30:70 EtOAc/hexane) showed a new spot at Rf=0.38 along with disappearance of starting material (Rf=0.35). The mixture was quenched with saturated NH$_4$Cl (100.0 ml), extracted with ethyl acetate (3×150 mL), washed with brine and dried (MgSO$_4$). The solvent was stripped off in vacuo to afford crude product (yellow oil) which was purified by flash column chromatography on a silica gel using 20% EtOAC/hexane to afford 12.3 g (mp 95–96° C., 43% yield) of desired product as white solid. $^1$H NMR (CDCl$_3$): 1.22–1.27 (t, 3H, CH$_3$), 2.74–2.81 (q, 2H, CH$_2$), 3.94–4.03 (m, 4H, 2×OCH$_2$), 4.59 (s, 2H, CH$_2$), 5.54 (s, 2H, CH$_2$), 6.62 (s, 1H, CH), 7.27–7.54 (m, 8H, aromatic). Mass spectrum (CI-NH$_3$): 461 (M$^+$). Anal. calcd. for C$_{23}$H$_{22}$N$_2$O$_4$Cl$_2$: C, 59.88; H, 4.82; N. 6.07. Found: C, 59.77; H, 4.78; N, 5.93.

Part E: 1-[(Benzyloxy)methyl]-4-(2,4-dichlorobenzoyl)-2-ethyl-5-formylimidazole: The above acetal (12.1 g, 0.0263 moles, Part D of Example 544) was dissolved in acetone (200.0 mL) and treated with 3.0 M aqeous HCl (400.0 mL) at room temperature. The reaction mixture was stirred for 24 h at this temperature and TLC (30:70 EtOAc/hexane) showed a new spot at Rf=0.55. It was then quenched with saturated NaCl (50.0 ml), extracted with ethyl acetate (3×150 mL), washed with brine and dried (MgSO$_4$). The solvent was removed in vacuum to afford yellow liquid and purified the crude by flash column chromatography on a silica gel using 15% EtOAC/hexane to afford 6.0 g (55% yield) of desired product as colorless oil. $^1$H NMR (CDCl$_3$): 1.27–1.32 (t, 3H, CH$_3$), 2.78–2.86 (q, 2H, CH$_2$), 4.62 (s, 2H, CH$_2$), 5.92 (s, 2H, CH$_2$), 7.25–7.55 (m, 8H, aromatic), 10.39 (s, 1H, CHO). Mass spectrum (CI-NH$_3$): 417 (M$^+$) Anal. calcd. for C$_{21}$H$_{18}$N$_2$O$_3$Cl$_2$: C, 60.44; H, 4.36; N, 6.71. Found: C, 60.43; H, 4.45; N, 6.49.

Part F: Methyl 1-[(Benzyloxy)methyl]-4-(2,4-dichlorobenzoyl)-2-ethyl-5-imidazole carboxylate: A mixture of 2-Et-5-CHO-imidazole derivative (6.0 g, fw=417, 14.34 mmoles, Part E of Example 544) in methanol (120 mL) was treated with NaCN (Aldrich, fw=49, 3.54 g, 12.0 mmoles, 5 equiv.), AcOH (Baker, fw=60, 1.38 g; 22.92 mmoles, 1.6 equiv.) and MnO$_2$, activated (Aldrich, fw=86.94, 25.8 g, 301.2 mmoles, 21 equiv.). The resulting mixture was stirred at room temp under nitrogen for 3 h. TLC (30:70 EtOAc/hexane) revealed absence of starting material at Rf=0.55 and showed a new spot at Rf=0.35. The reaction mixture was filtered through celite, washed with methanol, concentrated in vacuo. The residue was diluted with water, extracted with ethyl acetate, washed with brine, dried and concentrated in vacuo to afford yellow oil. The crude was purified by flash column chromatography on a silica gel using 30:70 EtOAc/hexane as eluent to afford 4.62 g (72% yield) of colorless oil. HRMS calcd. for C$_{22}$H$_{21}$Cl$_2$N$_2$O$_4$: 447.0878. Found: 447.0870 (M+H). Anal. calcd. for C$_{22}$H$_{20}$Cl$_2$N$_2$O$_4$: C, 59.07; H, 4.52; N, 6.26. Found: C, 58.97; H, 4.65; N, 6.07

Part G: 1-[(Benzyloxy)methyl]-4-(2,4-dichlorophenyl)-2-ethyl-imidazo[4,5-d]pyridazin-7-one: A mixture of imidazole deriv. (3.55 g, fw=447, 0.00794 moles, Part F of Example 544) in ethanol (50 mL) was treated with anhydrous hydrazine (3.3 g, 0.102 moles, 13 equiv) and refluxed under nitrogen for 2 h. TLC (30:70 EtOAc/hexane) revealed absence of starting material (Rf=0.35) and showed a new spot (Rf=0.27). The solvent was removed under vacuo and purified the crude titurating with 1:1 EtOH/hexane to afford 2.2 g (65% yield, mp 174–175° C.) of desired product as white solid. Mass spectrum (APcI): (m/z=429, M$^+$). Anal. calcd. for C$_{21}$H$_{18}$N$_4$Cl$_2$O$_2$: C, 58.75; H, 4.24; N, 13.05. Found: C, 58.65; H, 4.30; N, 12.86.

Part H: 1-[(Benzyloxy)methyl]-4-(2,4-dichlorophenyl)-2-ethyl-6-(N-methyl)-imidazo[4,5-d]pyridazin-7-one: To a solution of the above 6H-imidazo[4,5-d]pyridazin-7-one derivative (2.2 g, 0.005 moles, Part G of Example 544) in benzene (100 mL) was added powdered KOH (0.43 g, 0.0076 moles), n-Bu$_4$NBr (161 mg, 0.0005 moles ) and MeI (excess) at room temperature. The reaction mixture appeared white suspension and stirred for 48 h. TLC (30:70 EtOAc/hexane) showed a new spot at Rf=0.40 along with disappearance of starting material (Rf=0.27). The reaction mixture was diluted with EtOAc (50 mL), washed with brine (10 mL), dried with MgSO$_4$ and concentrated to a residue. The crude was purified by flash column chromatography on a silica gel using 25:75 EtOAc/hexane as eluent to afford 1.96 g (86% yield, mp 80–81° C.) of the product as white solid. Anal. calcd. for C$_{23}$H$_{20}$N$_4$Cl$_2$O$_2$: C, 59.60; H, 4.56; N, 12.64. Found: C, 59.61; H, 4.57; N, 12.52.

Part I: Title Compound: A mixture of 1-[(Benzyloxy)methyl]-4-(2,4-dichlorophenyl)-2-ethyl-6-(N-methyl)-imidazo[4,5-d]pyridazin-7-one (2.6 g, fw=443.33, 5.87 mmol, Part H of Example 544) in ethanol (100 mL) was treated with conc. HCl (2.93 mL, 29.3 mmol, 5.0 equiv) and refluxed under nitrogen for 60 mins. TLC (30:70 EtOAc/hexane) revealed disappearance of starting material (Rf=0.40) and a new spot appeared near the origin. The reaction mixture was cooled to room temperature adjusted the pH using NaHCO$_3$ and the solvent was removed under vacuo and purified the crude by flash column chromatography on a silica gel using 50% EtOAc/hexane to afford 1.85 g (mp 234–235° C., 97% yield) of desired product as white solid. NMR (CDCl$_3$): 1.46–1.52 (t, 3H, CH$_3$), 3.04–3.11 (q, 2H, CH$_2$), 4.04 (s, 3H, N-Me), 7.38–7.41 (d, 2H, aromatic), 7.54–7.57 (m, 3H, aromatic), 13.65 (bs, 1H, NH). Mass spectrum (CI-NH$_3$): m/z=323 (M$^+$). HRMS calcd. for C$_{14}$H$_{13}$N$_4$Cl$_2$O$_1$: 323.0466. Found:323.0477 (M+H). Anal. calcd. for C$_{14}$H$_{12}$N$_4$Cl$_2$O$_1$: C, 52.03; H, 3.74. Found: C, 51.92 ; H, 4.07.

Example 546

1-Butyl-4-(2,4-dichlorophenyl)-2-ethyl-6-(N-methyl)-imidazo[4,5-d]pyridazin-7-one To a solution of imidazopyridazin-7-one deriv. (32.3 mg, fw=323, 0.1 mmol, Part I of example 544) in DMF (2.0 mL) under nitrogen atmosphere was added 60% NaH in oil dispersion (6.0 mg, fw=24, 0.15 mmol, 1.5 equiv.). The mixture was stirred at room temp for 5 mins and then added 1-bromobutane (27.6 mg, fw=184, 0.15 mmol, 1.5 equiv) to reaction mixture and stirred overnight. TLC (30:70 EtOAc/ hexane) showed a new spot at Rf=0.36 along with disappearance of starting material (Rf=origin). The reaction mixture was diluted with water (5.0 mL), extracted with EtOAc (3*5 mL), washed with brine (10 mL), dried with MgSO$_4$ and concentrated to a residue. The crude was purified by flash column chromatography on a silica gel using 25:75 EtOAc/hexane as eluent to afford 29.7 mg (78% yield) of the product as colorless oil. HRMS calcd. for $C_{18}H_{21}N_4O_1Cl_2$: 379.1092. Found: 379.1086 (M+H)

Example 548

4-(2,4-dichlorophenyl)-2-ethyl-1-[1-(ethyl)pentyl)]-6-(N-methyl)-imidazo[4,5-d]pyridazin-7-one To a solution of imidazopyridazin-7-one deriv. (48.3 mg, fw=323, 0.15 mmol, Part I of Example 544) in THF (2.0 mL) under nitrogen atmosphere was added PPh$_3$ (43.3 mg, fw=262.29, 0.165 mmol, 1.1 equiv.), and 3-heptanol (21.0 mg, Aldrich, 0.18 mmol, fw=116.2, 1.2 equiv.). The mixture was cooled to −20° C. and then added diisopropylazodicarboxylate (33.3 microlit., Aldrich, 0.165 mmol, fw=202, 1.1 equiv.) dropwise using a syringe. The resultant mixture was stirred at −20° C. for 2 h followed by room temperature for 20 h. TLC (30:70 EtOAc/hexane) showed a new spot at Rf=0.53 along with trace amount of starting material (Rf=origin). The reaction mixture was concentrated to a residue. The crude was purified by flash column chromatography on a silica gel using 15:85 EtOAc/hexane as eluent to afford 37 mg (58% yield, 110–111° C.) of the product as white solid. HRMS calcd. for $C_{21}H_{27}N_4O_1Cl_2$: 421.1562. Found: 421.1555 (M+H).

TABLE 1

| Ex. | R$_3$ | R$_2$ | Ar | mp (° C.) |
|---|---|---|---|---|
| 2 | Me | 3-pentyl | 2,4-Cl$_2$—Ph | 94–95 |
| 3 | Et | 3-pentyl | 214-Cl$_2$—Ph | oil |
| 4 | Pr | 3-pentyl | 2,4-Cl$_2$—Ph | oil |
| 5 | CH$_2$-c-C$_3$H$_5$ | 3-pentyl | 2,4-Cl$_2$—Ph | oil |
| 6 | Me | 3-pentyl | 2,4-(CF$_3$)$_2$—Ph | 139–140 |
| 7 | Me | 2-pentyl | 2,4-Cl$_2$—Ph | 89–90 |
| 9 | Me | 2-pentyl | 2,5-(Me)$_2$-4-MeO-Ph | amorph. |
| 10 | Me | CH(Et)CH$_2$OH | 2,4-Cl$_2$—Ph | |
| 12 | Me | CH(Et)CH$_2$OMe | 2,4-Cl$_2$—Ph | |
| 13 | Me | CH(Et)CH$_2$CH$_2$OMe | 2,4-Cl$_2$—Ph | |
| 14 | Me | 2-butyl | 2,4-Cl$_2$—Ph | |
| 15 | Me | cyclobutyl | 2,4-Cl$_2$—Ph | oil |
| 16 | Me | cyclopentyl | 2,4-Cl$_2$—Ph | 180–181 |
| 17 | Me | CH(Me)cyclobutyl | 2,4-Cl$_2$—Ph | |
| 18 | Me | CH(Me)cyclopropyl | 2,4-Cl$_2$—Ph | oil |
| 19 | Me | CH(Et)cyclobutyl | 2,4-Cl$_2$—Ph | |
| 20 | Me | CH(Et)cyclopropyl | 2,4-Cl$_2$—Ph | 117–118 |
| 21 | Me | CH(Me)CH$_2$-cyclobutyl | 2,4-Cl$_2$—Ph | |
| 22 | Me | CH(OH)CH$_2$-cyclobutyl | 2,4-Cl$_2$—Ph | |
| 23 | Me | CH(Me)CH$_2$-cyclopropyl | 2,4-Cl$_2$—Ph | |
| 24 | Me | CH(Et)CH$_2$-cyclobutyl | 2,4-Cl$_2$—Ph | |
| 25 | Me | CH(Et)CH$_2$-cyclopropyl | 2,4-Cl$_2$—Ph | |
| 26 | Me | CH(CH$_2$OMe)cyclobutyl | 2,4-Cl$_2$—Ph | |
| 27 | Me | CH(CH$_2$OMe)cyclopropyl | 2,4-Cl$_2$—Ph | |
| 28 | Me | CH(CH$_2$OEt)cyclobutyl | 2,4-Cl$_2$—Ph | |
| 29 | Me | CH(CH$_2$OEt)cyclopropyl | 2,4-Cl$_2$—Ph | |
| 30 | Me | CH(cyclobutyl)$_2$ | 2,4-Cl$_2$—Ph | |
| 31 | Me | CH(cyclopropyl)$_2$ | 2,4-Cl$_2$—Ph | 140–142 |
| 32 | Me | CH(Et)CH$_2$CONMe$_2$ | 2,4-Cl$_2$—Ph | |
| 33 | Me | CH(Et)CH$_2$CH$_2$NMe$_2$ | 2,4-Cl$_2$—Ph | |
| 34 | Me | CH(CH$_2$OMe)Me | 2,4-Cl$_2$—Ph | |
| 35 | Me | CH(CH$_2$OMe)Et | 2,4-Cl$_2$—Ph | |
| 36 | Me | CH(CH$_2$OMe)Pr | 2,4-Cl$_2$—Ph | |
| 37 | Me | CH(CH$_2$OEt)Me | 2,4-Cl$_2$—Ph | |
| 38 | Me | CH(CH$_2$OEt)Et | 2,4-Cl$_2$—Ph | |
| 39 | Me | CH(CH$_2$OEt)Pr | 2,4-Cl$_2$—Ph | |
| 40 | Me | CH(CH$_2$C≡CMe)Et | 2,4-Cl$_2$—Ph | |
| 41 | Me | CH(CH$_2$CH═CHMe)Et | 2,4-Cl$_2$—Ph | |
| 42 | Me | CH(Et)CH$_2$OH | 2,4,6-Me$_3$-Ph | |
| 43 | Me | CH(Et)CH$_2$OMe | 2,4,6-Me$_3$-Ph | |
| 44 | Me | CH(Et)CH$_2$CH$_2$OMe | 2,4,6-Me$_3$-Ph | |
| 45 | Me | 3-pentyl | 2,4,6-Me$_3$-Ph | |
| 46 | Me | 2-pentyl | 2,4,6-Me$_3$-Ph | |
| 47 | Me | 2-butyl | 2,4,6-Me$_3$-Ph | |
| 48 | Me | cyclobutyl | 2,4,6-Me$_3$-Ph | |

TABLE 1-continued

Structure: 2-ethyl-imidazo pyridazinone core with $R^2$ on N, $NR^3$ adjacent to C=O, and Ar substituent.

| Ex. | $R_3$ | $R_2$ | Ar | mp (° C.) |
|---|---|---|---|---|
| 49 | Me | cyclopentyl | 2,4,6-Me$_3$-Ph | |
| 50 | Me | CH(Me)cyclobutyl | 2,4,6-Me$_3$-Ph | |
| 51 | Me | CH(Me)cyclopropyl | 2,4,6-Me$_3$-Ph | |
| 52 | Me | CH(OMe)cyclopropyl | 2,4,6-Me$_3$-Ph | |
| 53 | Me | CH(Et)cyclobutyl | 2,4,6-Me$_3$-Ph | |
| 54 | Me | CH(Et)cyclopropyl | 2,4,6-Me$_3$-Ph | |
| ss | Me | CH(Me)CH$_2$-cyclobutyl | 2,4,6-Me$_3$-Ph | |
| 56 | Me | CH(Me)CH$_2$-cyclopropyl | 2,4,6-Me$_3$-Ph | |
| 57 | Me | CH(OMe)CH$_2$-cyclopropyl | 2,4,6-Me$_3$-Ph | |
| 58 | Me | CH(Et)CH$_2$-cyclobutyl | 2,4,6-Me$_3$-Ph | |
| 59 | Me | CH(Et)CH$_2$-cyclopropyl | 2,4,6-Me$_3$-Ph | |
| 60 | Me | CH(CH$_2$OMe)cyclobutyl | 2,4,6-Me$_3$-Ph | |
| 61 | Me | CH(CH$_2$OMe)cyclopropyl | 2,4,6-Me$_3$-Ph | |
| 62 | Me | CH(CH$_2$OEt)cyclobutyl | 2,4,6-Me$_3$-Ph | |
| 63 | Me | CH(CH$_2$OEt)cyclopropyl | 2,4,6-Me$_3$-Ph | |
| 64 | Me | CH(cyclobutyl)$_2$ | 2,4,6-Me$_3$-Ph | |
| 65 | Me | CH(cyclopropyl)$_2$ | 2,4,6-Me$_3$-Ph | |
| 66 | Me | CH(Et)CH$_2$CONMe$_2$ | 2,4,6-Me$_3$-Ph | |
| 67 | Me | CH(Et)CH$_2$CH$_2$NMe$_2$ | 2,4,6-Me$_3$-Ph | |
| 68 | Me | CH(CH$_2$OMe)Me | 2,4,6-Me$_3$-Ph | |
| 69 | Me | CH(CH$_2$OMe)Et | 2,4,6-Me$_3$-Ph | |
| 70 | Me | CH(CH$_2$OMe)Pr | 2,4,6-Me$_3$-Ph | |
| 71 | Me | CH(CH$_2$OEt)Me | 2,4,6-Me$_3$-Ph | |
| 72 | Me | CH(CH$_2$OEt)Et | 2,4,6-Me$_3$-Ph | |
| 73 | Me | CH(CH$_2$OEt)Pr | 2,4,6-Me$_3$-Ph | |
| 74 | Me | CH(CH$_2$C≡CMe)Et | 2,4,6-Me$_3$-Ph | |
| 75 | Me | CH(CH$_2$CH=CHMe)Et | 2,4,6-Me$_3$-Ph | |
| 76 | Me | CH(Et)CH$_2$OH | 2,4-Me$_2$-Ph | |
| 77 | Me | CH(Et)CH$_2$OMe | 2,4-Me$_2$-Ph | |
| 78 | Me | CH(Et)CH$_2$CH$_2$OMe | 2,4-Me$_2$-Ph | |
| 79 | Me | 3-pentyl | 2,4-Me$_2$-Ph | |
| 80 | Me | 2-pentyl | 2,4-Me$_2$-Ph | |
| 81 | Me | 2-butyl | 2,4-Me$_2$-Ph | |
| 82 | Me | cyclobutyl | 2,4-Me$_2$-Ph | |
| 83 | Me | cyclopentyl | 2,4-Me$_2$-Ph | |
| 84 | Me | CH(Me)cyclobutyl | 2,4-Me$_2$-Ph | |
| 85 | Me | CH(OH)cyclobutyl | 2,4-Me$_2$-Ph | |
| 86 | Me | CH(Me)cyclopropyl | 2,4-Me$_2$-Ph | |
| 87 | Me | CH(OH)cyclopropyl | 2,4-Me$_2$-Ph | |
| 88 | Me | CH(Et)cyclobutyl | 2,4-Me$_2$-Ph | |
| 89 | Me | CH(Et)cyclopropyl | 2,4-Me$_2$-Ph | |
| 90 | Me | CH(Me)CH$_2$-cyclobutyl | 2,4-Me$_2$-Ph | |
| 91 | Me | CH(Me)CH$_2$-cyclopropyl | 2,4-Me$_2$-Ph | |
| 92 | Me | CH(OMe)CH$_2$-cyclopropyl | 2,4-Me$_2$-Ph | |
| 93 | Me | CH(Et)CH$_2$-cyclobutyl | 2,4-Me$_2$-Ph | |
| 94 | Me | CH(Et)CH$_2$-cyclopropyl | 2,4-Me$_2$-Ph | |
| 9s | Me | CH(CH$_2$OMe)cyclobutyl | 2,4-Me$_2$-Ph | |
| 96 | Me | CH(CH$_2$OMe)cyclopropyl | 2,4-Me$_2$-Ph | |
| 97 | Me | CH(CH$_2$OEt)cyclobutyl | 2,4-Me$_2$-Ph | |
| 98 | Me | CH(CH$_2$OEt)cyclopropyl | 2,4-Me$_2$-Ph | |
| 99 | Me | CH(cyclobutyl)$_2$ | 2,4-Me$_2$-Ph | |
| 100 | Me | CH(cyclopropyl)$_2$ | 2,4-Me$_2$-Ph | |
| 101 | Me | CH(Et)CH$_2$CONMe$_2$ | 2,4-Me$_2$-Ph | |
| 102 | Me | CH(Et)CH$_2$NMe$_2$ | 2,4-Me$_2$-Ph | |
| 103 | Me | CH(CH$_2$OMe)Me | 2,4-Me$_2$-Ph | |
| 104 | Me | CH(CH$_2$OMe)Et | 2,4-Me$_2$-Ph | |
| 105 | Me | CH(CH$_2$OMe)Pr | 2,4-Me$_2$-Ph | |
| 106 | Me | CH(CH$_2$OEt)Me | 2,4-Me$_2$-Ph | |
| 107 | Me | CH(CH$_2$OEt)Et | 2,4-Me$_2$-Ph | |
| 108 | Me | CH(CH$_2$OEt)Pr | 2,4-Me$_2$-Ph | |
| 109 | Me | CH(CH$_2$C≡CMe)Et | 2,4-Me$_2$-Ph | |
| 110 | Me | CH(CH$_2$C≡CMe)Et | 2,4-Me$_2$-Ph | |
| 111 | Me | CH(Et)CH$_2$OH | 2-Me-4-MeO—Ph | |
| 112 | Me | CH(Et)CH$_2$Me | 2-Me-4-MeO—Ph | |
| 113 | Me | CH(Et)CH$_2$CH$_2$OMe | 2-Me-4-MeO—Ph | |
| 114 | Me | 3-pentyl | 2-Me-4-MeO—Ph | 125–126 |

TABLE 1-continued

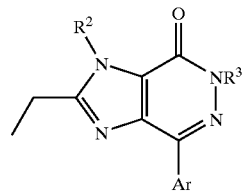

| Ex. | R₃ | R₂ | Ar | mp (° C.) |
|---|---|---|---|---|
| 115 | Me | 2-pentyl | 2-Me-4-MeO—Ph | oil |
| 116 | Me | 2-butyl | 2-Me-4-MeO—Ph | |
| 117 | Me | cyclobutyl | 2-Me-4-MeO—Ph | |
| 118 | Me | cyclopentyl | 2-Me-4-MeO—Ph | |
| 119 | Me | CH(Me)cyclobutyl | 2-Me-4-MeO—Ph | |
| 120 | Me | CH(Me)cyclopropyl | 2-Me-4-MeO—Ph | |
| 121 | Me | CH(Et)cyclobutyl | 2-Me-4-MeO—Ph | |
| 122 | Me | CH(Et)cyclopropyl | 2-Me-4-MeO—Ph | |
| 123 | Me | CH(Me)CH₂-cyclobutyl | 2-Me-4-MeO—Ph | |
| 124 | Me | CH(Me)CH₂-cyclopropyl | 2-Me-4-MeO—Ph | |
| 125 | Me | CH(Et)CH₂-cyclobutyl | 2-Me-4-MeO—Ph | |
| 126 | Me | CH(Et)CH₂-cyclopropyl | 2-Me-4-MeO—Ph | |
| 127 | Me | CH(CH₂OMe)cyclobutyl | 2-Me-4-MeO—Ph | |
| 128 | Me | CH(CH₂OMe)cyclopropyl | 2-Me-4-MeO—Ph | |
| 129 | Me | CH(CH₂OEt)cyclobutyl | 2-Me-4-MeO—Ph | |
| 130 | Me | CH(CH₂OEt)cyclopropyl | 2-Me-4-MeO—Ph | |
| 131 | Me | CH(cyclobutyl)₂ | 2-Me-4-MeO—Ph | |
| 132 | Me | CH(cyclopropyl)₂ | 2-Me-4-MeO—Ph | |
| 133 | Me | CH(Et)CH₂CONMe₂ | 2-Me-4-MeO—Ph | |
| 134 | Me | CH(Et)CH₂CH₂NMe₂ | 2-Me-4-MeO—Ph | |
| 135 | Me | CH(CH₂OMe)Me | 2-Me-4-MeO—Ph | |
| 136 | Me | CH(CH₂OMe)Et | 2-Me-4-MeO—Ph | |
| 137 | Me | CH(CH₂OMe)Pr | 2-Me-4-MeO—Ph | |
| 138 | Me | CH(CH₂OEt)Me | 2-Me-4-MeO—Ph | |
| 139 | Me | CH(CH₂OEt)Et | 2-Me-4-MeO—Ph | |
| 140 | Me | CH(CH₂OEt)Pr | 2-Me-4-MeO—Ph | |
| 141 | Me | CH(CH₂C≡CMe)Et | 2-Me-4-MeO—Ph | |
| 142 | Me | CH(CH₂CH=CHMe)Et | 2-Me-4-MeO—Ph | |
| 143 | Me | CH(Et)CH₂OH | 2-Cl-4-MeO—Ph | |
| 144 | Me | CH(Et)CH₂OMe | 2-Cl-4-MeO—Ph | |
| 145 | Me | CH(Et)CH₂CH₂OMe | 2-Cl-4-MeO—Ph | |
| 146 | Me | 3-pentyl | 2-Cl-4-MeO—Ph | |
| 147 | Me | 2-pentyl | 2-Cl-4-MeO—Ph | 112–113 |
| 148 | Me | 2-butyl | 2-Cl-4-MeO—Ph | |
| 149 | Me | cyclobutyl | 2-Cl-4-MeO—Ph | |
| 150 | Me | cyclopentyl | 2-Cl-4-MeO—Ph | |
| 151 | Me | CH(Me)cyclobutyl | 2-Cl-4-MeO—Ph | |
| 152 | Me | CH(Me)cyclopropyl | 2-Cl-4-MeO—Ph | |
| 153 | Me | CH(Et)cyclobutyl | 2-Cl-4-MeO—Ph | |
| 154 | Me | CH(Et)cyclopropyl | 2-Cl-4-MeO—Ph | |
| 155 | Me | CH(Me)CH₂-cyclobutyl | 2-Cl-4-MeO—Ph | |
| 156 | Me | CH(Me)CH₂-cyclopropyl | 2-Cl-4-MeO—Ph | |
| 157 | Me | CH(Et)CH₂-cyclobutyl | 2-Cl-4-MeO—Ph | |
| 158 | Me | CH(Et)CH₂-cyclopropyl | 2-Cl-4-MeO—Ph | |
| 159 | Me | CH(CH₂OMe)cyclobutyl | 2-Cl-4-MeO—Ph | |
| 160 | Me | CH(CH₂OMe)cyclopropyl | 2-Cl-4-MeO—Ph | |
| 161 | Me | CH(CH₂OEt)cyclobutyl | 2-Cl-4-MeO—Ph | |
| 162 | Me | CH(CH₂OEt)cyclopropyl | 2-Cl-4-MeO—Ph | |
| 163 | Me | CH(cyclobutyl)₂ | 2-Cl-4-MeO—Ph | |
| 164 | Me | CH(cyclopropyl)₂ | 2-Cl-4-MeO—Ph | |
| 165 | Me | CH(Et)CH₂CONMe₂ | 2-Cl-4-MeO—Ph | |
| 166 | Me | CH(Et)CH₂CH₂NMe₂ | 2-Cl-4-MeO—Ph | |
| 167 | Me | CH(CH₂OMe)Me | 2-Cl-4-MeO—Ph | |
| 168 | Me | CH(CH₂ONe)Et | 2-Cl-4-MeO—Ph | |
| 169 | Me | CH(CH₂OMe)Pr | 2-Cl-4-MeO—Ph | |
| 170 | Me | CH(CH₂OEt)Me | 2-Cl-4-MeO—Ph | |
| 171 | Me | CH(CH₂OEt)Et | 2-Cl-4-MeO—Ph | |
| 172 | Me | CH(CH₂OEt)Pr | 2-Cl-4-MeO—Ph | |
| 173 | Me | CH(CH₂C≡CMe)Et | 2-Cl-4-MeO—Ph | |
| 174 | Me | CH(CH₂CH=CHMe)Et | 2-Cl-4-MeO—Ph | |
| 175 | Me | CH(Et)CH₂OH | 2-Cl-4,5-(MeO)₂-Ph | |
| 176 | Me | CH(Et)CH₂OMe | 2-Cl-4,5-(MeO)₂-Ph | |
| 177 | Me | CH(Et)CH₂CH₂OMe | 2-Cl-4,5-(MeO)₂-Ph | |
| 178 | Me | 3-pentyl | 2-Cl-4,5-(MeO)₂-Ph | |
| 179 | Me | 2-pentyl | 2-Cl-4,5-(MeO)₂-Ph | |
| 180 | Me | 2-butyl | 2-Cl-4,5-(MeO)₂-Ph | |

TABLE 1-continued

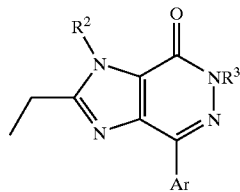

| Ex. | R$_3$ | R$_2$ | Ar | mp (° C.) |
|---|---|---|---|---|
| 181 | Me | cyclobutyl | 2-Cl-4,5-(MeO)$_2$-Ph | |
| 182 | Me | cyclopentyl | 2-Cl-4,5-(MeO)$_2$-Ph | |
| 183 | Me | CH(Me)cyclobutyl | 2-Cl-4,5-(MeO)$_2$-Ph | |
| 184 | Me | CH(Me)cyclopropyl | 2-Cl-4,5-(MeO)$_2$-Ph | |
| 185 | Me | CH(Et)cyclobutyl | 2-Cl-4,5-(MeO)$_2$-Ph | |
| 186 | Me | CH(Et)cyclopropyl | 2-Cl-4,5-(MeO)$_2$-Ph | |
| 187 | Me | CH(Me)CH$_2$-cyclobutyl | 2-Cl-4,5-(MeO)$_2$-Ph | |
| 188 | Me | CH(Me)CH$_2$-cyclopropyl | 2-Cl-4,5-(MeO)$_2$-Ph | |
| 189 | Me | CH(Et)CH$_2$-cyclobutyl | 2-Cl-4,5-(MeO)$_2$-Ph | |
| 190 | Me | CH(Et)CH$_2$-cyclopropyl | 2-Cl-4,5-(MeO)$_2$-Ph | |
| 191 | Me | CH(CH$_2$OMe)cyclobutyl | 2-Cl-4,5-(MeO)$_2$-Ph | |
| 192 | Me | CH(CH$_2$OMe)cyclopropyl | 2-Cl-4,5-(MeO)$_2$-Ph | |
| 193 | Me | CH(CH$_2$OEt)cyclobutyl | 2-Cl-4,5-(MeO)$_2$-Ph | |
| 194 | Me | CH(CH$_2$OEt)cyclopropyl | 2-Cl-4,5-(MeO)$_2$-Ph | |
| 195 | Me | CH(cyclobutyl)$_2$ | 2-Cl-4,5-(MeO)$_2$-Ph | |
| 196 | Me | CH(cyclopropyl)$_2$ | 2-Cl-4,5-(MeO)$_2$-Ph | |
| 197 | Me | CH(Et)CH$_2$CONMe$_2$ | 2-Cl-4,5-(MeO)$_2$-Ph | |
| 198 | Me | CH(Et)CH$_2$CH$_2$NMe$_2$ | 2-Cl-4,5-(MeO)$_2$-Ph | |
| 199 | Me | CH(CH$_2$OMe)Me | 2-Cl-4,5-(MeO)$_2$-Ph | |
| 200 | Me | CH(CH$_2$OMe)Et | 2-Cl-4,5-(MeO)$_2$-Ph | |
| 201 | Me | CH(CH$_2$OMe)Pr | 2-Cl-4,5-(MeO)$_2$-Ph | |
| 202 | Me | CH(CH$_2$OEt)Me | 2-Cl-4,5-(MeO)$_2$-Ph | |
| 203 | Me | CH(CH$_2$OEt)Et | 2-Cl-4,5-(MeO)$_2$-Ph | |
| 204 | Me | CH(CH$_2$OEt)Pr | 2-Cl-4,5-(MeO)$_2$-Ph | |
| 205 | Me | CH(CH$_2$C≡CMe)Et | 2-Cl-4,5-(MeO)$_2$-Ph | |
| 206 | Me | CH(CH$_2$CH=CHMe)Et | 2-Cl-4,5-(MeO)$_2$-Ph | |
| 207 | Me | CH(Et)CH$_2$OH | 2-Cl-4-MeO-5-F—Ph | |
| 208 | Me | CH(Et)CH$_2$OMe | 2-Cl-4-MeO-5-F—Ph | |
| 209 | Me | CH(Et)CH$_2$CH$_2$OMe | 2-Cl-4-MeO-5-F—Ph | |
| 210 | Me | 3-pentyl | 2-Cl-4-MeO-5-F—Ph | |
| 211 | Me | 2-pentyl | 2-Cl-4-MeO-5-F—Ph | |
| 212 | Me | 2-butyl | 2-Cl-4-MeO-5-F—Ph | |
| 213 | Me | cyclobutyl | 2-Cl-4-MeO-5-F—Ph | |
| 214 | Me | cyclopentyl | 2-Cl-4-MeO-5-F—Ph | |
| 215 | Me | CH(Me)cyclobutyl | 2-Cl-4-MeO-5-F—Ph | |
| 216 | Me | CH(Me)cyclopropyl | 2-Cl-4-MeO-5-F—Ph | |
| 217 | Me | CH(Et)cyclobutyl | 2-Cl-4-MeO-5-F—Ph | |
| 218 | Me | CH(Et)cyclopropyl | 2-Cl-4-MeO-5-F—Ph | |
| 219 | Me | CH(OEt)cyclobutyl | 2-Cl-4-MeO-5-F—Ph | |
| 220 | Me | CH(Me)CH$_2$-cyclobutyl | 2-Cl-4-MeO-5-F—Ph | |
| 221 | Me | CH(Me)CH$_2$-cyclopropyl | 2-Cl-4-MeO-5-F—Ph | |
| 222 | Me | CH(Et)CH$_2$-cyclobutyl | 2-Cl-4-MeO-5-F—Ph | |
| 223 | Me | CH(Et)CH$_2$-cyclopropyl | 2-Cl-4-MeO-5-F—Ph | |
| 224 | Me | CH(CH$_2$OMe)cyclobutyl | 2-Cl-4-MeO-5-F—Ph | |
| 225 | Me | CH(CH$_2$OMe)cyclopropyl | 2-Cl-4-MeO-5-F—Ph | |
| 226 | Me | CH(CH$_2$OEt)cyclobutyl | 2-Cl-4-MeO-5-F—Ph | |
| 227 | Me | CH(CH$_2$OEt)cyclopropyl | 2-Cl-4-MeO-5-F—Ph | |
| 228 | Me | CH(cyclobutyl)$_2$ | 2-Cl-4-MeO-5-F—Ph | |
| 229 | Me | CH(cyclopropyl)$_2$ | 2-Cl-4-MeO-5-F—Ph | |
| 230 | Me | CH(Et)CH$_2$CONMe$_2$ | 2-Cl-4-MeO-5-F—Ph | |
| 231 | Me | CH(Et)CH$_2$CH$_2$NMe$_2$ | 2-Cl-4-MeO-5-F—Ph | |
| 232 | Me | CH(CH$_2$OMe)Me | 2-Cl-4-MeO-5-F—Ph | |
| 233 | Me | CH(CH$_2$OMe)Et | 2-Cl-4-MeO-5-F—Ph | |
| 234 | Me | CH(CH$_2$OMe)Pr | 2-Cl-4-MeO-5-F—Ph | |
| 234 | Me | CH(CH$_2$OEt)Me | 2-Cl-4-MeO-5-F—Ph | |
| 235 | Me | CH(CH$_2$OEt)Et | 2-Cl-4-MeO-5-F—Ph | |
| 236 | Me | CH(CH$_2$OEt)Pr | 2-Cl-4-MeO-5-F—Ph | |
| 237 | Me | CH(CH$_2$C≡CMe)Et | 2-Cl-4-MeO-5-F—Ph | |
| 238 | Me | CH(CH$_2$CH=CHMe)Et | 2-Cl-4-MeO-5-F—Ph | |
| 239 | Me | CH(Et)CH$_2$OH | 2-Me-4-MeO-5-F—Ph | |
| 240 | Me | CH(Et)CH$_2$OMe | 2-Me-4-MeO-5-F—Ph | |
| 241 | Me | CH(Et)CH$_2$CH$_2$OMe | 2-Me-4-MeO-5-F—Ph | |
| 242 | Me | 3-pentyl | 2-Me-4-MeO-5-F—Ph | |
| 243 | Me | 2-pentyl | 2-Me-4-MeO-5-F—Ph | |
| 244 | Me | 2-butyl | 2-Me-4-MeO-5-F—Ph | |
| 245 | Me | cyclobutyl | 2-Me-4-MeO-5-F—Ph | |

TABLE 1-continued

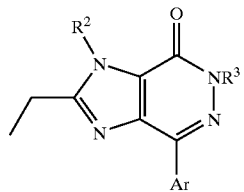

| Ex. | $R_3$ | $R_2$ | Ar | mp (° C.) |
|---|---|---|---|---|
| 246 | Me | cyclopentyl | 2-Me-4-MeO-5-F—Ph | |
| 247 | Me | CH(Me)cyclobutyl | 2-Me-4-MeO-5-F—Ph | |
| 248 | Me | CH(Me)cyclopropyl | 2-Me-4-MeO-5-F—Ph | |
| 249 | Me | CH(OMe)cyclopropyl | 2-Me-4-MeO-5-F—Ph | |
| 250 | Me | CH(Et)cyclobutyl | 2-Me-4-MeO-5-F—Ph | |
| 251 | Me | CH(Et)cyclopropyl | 2-Me-4-MeO-5-F—Ph | |
| 252 | Me | CH(Me)CH$_2$-cyclobutyl | 2-Me-4-MeO-5-F—Ph | |
| 253 | Me | CH(OMe)CH$_2$-cyclobutyl | 2-Me-4-MeO-5-F—Ph | |
| 254 | Me | CH(OH)CH$_2$-cyclobutyl | 2-Me-4-MeO-5-F—Ph | |
| 255 | Me | CH(Me)CH$_2$-cyclopropyl | 2-Me-4-MeO-5-F—Ph | |
| 256 | Me | CH(Et)CH$_2$-cyclobutyl | 2-Me-4-MeO-5-F—Ph | |
| 257 | Me | CH(Et)CH$_2$-cyclopropyl | 2-Me-4-MeO-5-F—Ph | |
| 258 | Me | CH(OMe)CH$_2$-cyclobutyl | 2-Me-4-MeO-5-F—Ph | |
| 259 | Me | CH(OMe)CH$_2$-cyclopropyl | 2-Me-4-MeO-5-F—Ph | |
| 260 | Me | CH(OEt)CH$_2$-cyclobutyl | 2-Me-4-MeO-5-F—Ph | |
| 261 | Me | CH(OEt)CH$_2$-cyclopropyl | 2-Me-4-MeO-5-F—Ph | |
| 262 | Me | CH(CH$_2$OMe)cyclobutyl | 2-Me-4-MeO-5-F—Ph | |
| 263 | Me | CH(CH$_2$OMe)cyclopropyl | 2-Me-4-MeO-5-F—Ph | |
| 264 | Me | CH(CH$_2$OEt)cyclobutyl | 2-Me-4-MeO-5-F—Ph | |
| 265 | Me | CH(CH$_2$OEt)cyclopropyl | 2-Me-4-MeO-5-F—Ph | |
| 266 | Me | CH(cyclobutyl)$_2$ | 2-Me-4-MeO-5-F—Ph | |
| 267 | Me | CH(cyclopropyl)$_2$ | 2-Me-4-MeO-5-F—Ph | |
| 268 | Me | CH(Et)CH$_2$CONMe$_2$ | 2-Me-4-MeO-5-F—Ph | |
| 269 | Me | CH(Et)CH$_2$CH$_2$NMe$_2$ | 2-Me-4-MeO-5-F—Ph | |
| 270 | Me | CH(CH$_2$OMe)Me | 2-Me-4-MeO-5-F—Ph | |
| 271 | Me | CH(CH$_2$OMe)Et | 2-Me-4-MeO-5-F—Ph | |
| 272 | Me | CH(CH$_2$OMe)Pr | 2-Me-4-MeO-5-F—Ph | |
| 273 | Me | CH(CH$_2$OEt)Me | 2-Me-4-MeO-5-F—Ph | |
| 274 | Me | CH(CH$_2$OEt)Et | 2-Me-4-MeO-5-F—Ph | |
| 275 | Me | CH(CH$_2$OEt)Pr | 2-Me-4-MeO-5-F—Ph | |
| 276 | Me | CH(CH$_2$C≡CMe)Et | 2-Me-4-MeO-5-F—Ph | |
| 277 | Me | CH(CH$_2$C≡CMe)Et | 2-Me-4-MeO-5-F—Ph | |
| 278 | Me | CH(Et)CH$_2$OH | 2,5-(Me)$_2$-4-MeO—Ph | |
| 279 | Me | CH(Et)CH$_2$OMe | 2,5-(Me)$_2$-4-MeO—Ph | |
| 280 | Me | CH(Et)CH$_2$CH$_2$OMe | 2,5-(Me)$_2$-4-MeO—Ph | |
| 281 | Me | 3-pentyl | 2,5-(Me)$_2$-4-MeO—Ph | |
| 282 | Me | 2-butyl | 2,5-(Me)$_2$-4-MeO—Ph | |
| 283 | Me | cyclobutyl | 2,5-(Me)$_2$-4-MeO—Ph | |
| 284 | Me | cyclopentyl | 2,5-(Me)$_2$-4-MeO—Ph | |
| 285 | Me | CH(Me)cyclobutyl | 2,5-(Me)$_2$-4-MeO—Ph | |
| 286 | Me | CH(Me)cyclopropyl | 2,5-(Me)$_2$-4-MeO—Ph | |
| 287 | Me | CH(Et)cyclobutyl | 2,S-(Me)$_2$-4-MeO—Ph | |
| 288 | Me | CH(Et)cyclopropyl | 2,5-(Me)$_2$-4-MeO—Ph | |
| 289 | Me | CH(Me)CH$_2$-cyclobutyl | 2,5-(Me)$_2$-4-MeO—Ph | |
| 290 | Me | CH(Me)CH$_2$-cyclopropyl | 2,5-(Me)$_2$-4-MeO—Ph | |
| 291 | Me | CH(Et)CH$_2$-cyclobutyl | 2,5-(Me)$_2$-4-MeO—Ph | |
| 292 | Me | CH(Et)CH$_2$-cyclopropyl | 2,5-(Me)$_2$-4-MeO—Ph | |
| 293 | Me | CH(CH$_2$OMe)cyclobutyl | 2,5-(Me)$_2$-4-MeO—Ph | |
| 294 | Me | CH(CH$_2$OMe)cyclopropyl | 2,5-(Me)$_2$-4-MeO—Ph | |
| 295 | Me | CH(CH$_2$OEt)cyclobutyl | 2,5-(Me)$_2$-4-MeO—Ph | |
| 296 | Me | CH(CH$_2$OEt)cyclopropyl | 2,5-(Me)$_2$-4-MeO—Ph | |
| 297 | Me | CH(cyclobutyl)$_2$ | 2,5-(Me)$_2$-4-MeO—Ph | |
| 298 | Me | CH(cyclopropyl)$_2$ | 2,5-(Me)$_2$-4-MeO—Ph | |
| 299 | Me | CH(Et)CH$_2$CONMe$_2$ | 2,5-(Me)$_2$-4-MeO—Ph | |
| 300 | Me | CH(Et)CH$_2$CH$_2$NMe$_2$ | 2,5-(Me)$_2$-4-MeO—Ph | |
| 301 | Me | CH(CH$_2$OMe)Me | 2,5-(Me)$_2$-4-MeO—Ph | |
| 302 | Me | CH(CH$_2$OMe)Et | 2,5-(Me)$_2$-4-MeO—Ph | |
| 303 | Me | CH(CH$_2$OMe)Pr | 2,5-(Me)$_2$-4-MeO—Ph | |
| 304 | Me | CH(CH$_2$OEt)Me | 2,5-(Me)$_2$-4-MeO—Ph | |
| 305 | Me | CH(CH$_2$OEt)Et | 2,5-(Me)$_2$-4-MeO—Ph | |
| 306 | Me | CH(CH$_2$OEt)Pr | 2,5-(Me)$_2$-4-MeO—Ph | |
| 307 | Me | CH(CH$_2$C≡CMe)Et | 2,5-(Me)$_2$-4-MeO—Ph | |
| 308 | Me | CH(CH$_2$CH═CHMe)Et | 2,5-(Me)$_2$-4-MeO—Ph | |
| 309 | Me | CH(Et)CH$_2$OH | 2-Me-6-Me$_2$N-pyrid-3-yl | |
| 310 | Me | CH(Et)CH$_2$OMe | 2-Me-6-Me$_2$N-pyrid-3-yl | |
| 311 | Me | CH(Et)CH$_2$CH$_2$OMe | 2-Me-6-Me$_2$N-pyrid-3-yl | |

TABLE 1-continued

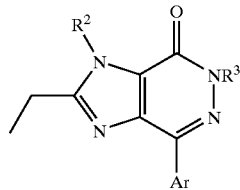

| Ex. | R$_3$ | R$_2$ | Ar | mp (° C.) |
|---|---|---|---|---|
| 312 | Me | 3-pentyl | 2-Me-6-Me$_2$N-pyrid-3-yl | |
| 313 | Me | 2-pentyl | 2-Me-6-Me$_2$N-pyrid-3-yl | |
| 314 | Me | 2-butyl | 2-Me-6-Me$_2$N-pyrid-3-yl | |
| 315 | Me | cyclobutyl | 2-Me-6-Me$_2$N-pyrid-3-yl | |
| 316 | Me | cyclopentyl | 2-Me-6-Me$_2$N-pyrid-3-yl | |
| 317 | Me | CH(Me)cyclobutyl | 2-Me-6-Me$_2$N-pyrid-3-yl | |
| 318 | Me | CH(Me)cyclopropyl | 2-Me-6-Me$_2$N-pyrid-3-yl | |
| 319 | Me | CH(Et)cyclobutyl | 2-Me-6-Me$_2$N-pyrid-3-yl | |
| 320 | Me | CH(Et)cyclopropyl | 2-Me-6-Me$_2$N-pyrid-3-yl | |
| 321 | Me | CH(Me)CH$_2$-cyclobutyl | 2-Me-6-Me$_2$N-pyrid-3-yl | |
| 322 | Me | CH(Me)CH$_2$-cyclopropyl | 2-Me-6-Me$_2$N-pyrid-3-yl | |
| 323 | Me | CH(Et)CH$_2$-cyclobutyl | 2-Me-6-Me$_2$N-pyrid-3-yl | |
| 324 | Me | CH(Et)CH$_2$-cyclopropyl | 2-Me-6-Me$_2$N-pyrid-3-yl | |
| 325 | Me | CH(CH$_2$OMe)cyclobutyl | 2-Me-6-Me$_2$N-pyrid-3-yl | |
| 326 | Me | CH(CH$_2$OMe)cyclopropyl | 2-Me-6-Me$_2$N-pyrid-3-yl | |
| 327 | Me | CH(CH$_2$OEt)cyclobutyl | 2-Me-6-Me$_2$N-pyrid-3-yl | |
| 328 | Me | CH(CH$_2$OEt)cyclopropyl | 2-Me-6-Me$_2$N-pyrid-3-yl | |
| 329 | Me | CH(cyclobutyl)$_2$ | 2-Me-6-Me$_2$N-pyrid-3-yl | |
| 330 | Me | CH(cyclopropyl)$_2$ | 2-Me-6-Me$_2$N-pyrid-3-yl | |
| 331 | Me | CH(Et)CH$_2$CONMe$_2$ | 2-Me-6-Me$_2$N-pyrid-3-yl | |
| 332 | Me | CH(Et)CH$_2$CH$_2$NMe$_2$ | 2-Me-6-Me$_2$N-pyrid-3-yl | |
| 333 | Me | CH(CH$_2$OMe)Me | 2-Me-6-Me$_2$N-pyrid-3-yl | |
| 334 | Me | CH(CH$_2$OMe)Et | 2-Me-6-Me$_2$N-pyrid-3-yl | |
| 335 | Me | CH(CH$_2$OMe)Pr | 2-Me-6-Me$_2$N-pyrid-3-yl | |
| 336 | Me | CH(CH$_2$OEt)Me | 2-Me-6-Me$_2$N-pyrid-3-yl | |
| 337 | Me | CH(CH$_2$OEt)Et | 2-Me-6-Me$_2$N-pyrid-3-yl | |
| 338 | Me | CH(CH$_2$OEt)Pr | 2-Me-6-Me$_2$N-pyrid-3-yl | |
| 339 | Me | CH(CH$_2$C≡CMe)Et | 2-Me-6-Me$_2$N-pyrid-3-yl | |
| 340 | Me | CH(CH$_2$CH=CHMe)Et | 2-Me-6-Me$_2$N-pyrid-3-yl | |
| 341 | Me | CH(Et)CH$_2$OH | 4-Me-2-Me$_2$N-pyrid-5-yl | |
| 342 | Me | CH(Et)CH$_2$OMe | 4-Me-2-Me$_2$N-pyrid-5-yl | |
| 343 | Me | CH(Et)CH$_2$CH$_2$OMe | 4-Me-2-Me$_2$N-pyrid-5-yl | |
| 344 | Me | 3-pentyl | 4-Me-2-Me$_2$N-pyrid-5-yl | |
| 345 | Me | 2-pentyl | 4-Me-2-Me$_2$N-pyrid-5-yl | |
| 346 | Me | 2-butyl | 4-Me-2-Me$_2$N-pyrid-5-yl | |
| 347 | Me | cyclobutyl | 4-Me-2-Me$_2$N-pyrid-5-yl | |
| 348 | Me | cyclopentyl | 4-Me-2-Me$_2$N-pyrid-5-yl | |
| 349 | Me | CH(Me)cyclobutyl | 4-Me-2-Me$_2$N-pyrid-5-yl | |
| 350 | Me | CH(Me)cyclopropyl | 4-Me-2-Me$_2$N-pyrid-5-yl | |
| 351 | Me | CH(Et)cyclobutyl | 4-Me-2-Me$_2$N-pyrid-5-yl | |
| 352 | Me | CH(Et)cyclopropyl | 4-Me-2-Me$_2$N-pyrid-5-yl | |
| 353 | Me | CH(Me)CH$_2$-cyclobutyl | 4-Me-2-Me$_2$N-pyrid-5-yl | |
| 354 | Me | CH(Me)CH$_2$-cyclopropyl | 4-Me-2-Me$_2$N-pyrid-5-yl | |
| 355 | Me | CH(Et)CH$_2$-cyclobutyl | 4-Me-2-Me$_2$N-pyrid-5-yl | |
| 356 | Me | CH(Et)CH$_2$-cyclopropyl | 4-Me-2-Me$_2$N-pyrid-5-yl | |
| 357 | Me | CH(CH$_2$OMe)cyclobutyl | 4-Me-2-Me$_2$N-pyrid-5-yl | |
| 358 | Me | CH(CH$_2$OMe)cyclopropyl | 4-Me-2-Me$_2$N-pyrid-5-yl | |
| 359 | Me | CH(CH$_2$OEt)cyclobutyl | 4-Me-2-Me$_2$N-pyrid-5-yl | |
| 360 | Me | CH(CH$_2$OEt)cyclopropyl | 4-Me-2-Me$_2$N-pyrid-5-yl | |
| 361 | Me | CH(cyclobutyl)$_2$ | 4-Me-2-Me$_2$N-pyrid-5-yl | |
| 362 | Me | CH(cyclopropyl)$_2$ | 4-Me-2-Me$_2$N-pyrid-5-yl | |
| 363 | Me | CH(Et)CH$_2$CONMe$_2$ | 4-Me-2-Me$_2$N-pyrid-5-yl | |
| 364 | Me | CH(Et)CH$_2$CH$_2$NMe$_2$ | 4-Me-2-Me$_2$N-pyrid-5-yl | |
| 365 | Me | CH(CH$_2$OMe)Me | 4-Me-2-Me$_2$N-pyrid-5-yl | |
| 366 | Me | CH(CH$_2$OMe)Et | 4-Me-2-Me$_2$N-pyrid-5-yl | |
| 367 | Me | CH(CH$_2$OMe)Pr | 4-Me-2-Me$_2$N-pyrid-5-yl | |
| 368 | Me | CH(CH$_2$OEt)Me | 4-Me-2-Me$_2$N-pyrid-5-yl | |
| 369 | Me | CH(CH$_2$OEt)Et | 4-Me-2-Me$_2$N-pyrid-5-yl | |
| 370 | Me | CH(CH$_2$OEt)Pr | 4-Me-2-Me$_2$N-pyrid-5-yl | |
| 371 | Me | CH(CH$_2$C≡CMe)Et | 4-Me-2-Me$_2$N-pyrid-5-yl | |
| 372 | Me | CH(CH$_2$CH=CHMe)Et | 4-Me-2-Me$_2$N-pyrid-5-yl | |
| 373 | Me | CH(Et)CH$_2$OH | 2-Me-6-MeO-pyrid-3-yl | |
| 374 | Me | CH(Et)CH$_2$OMe | 2-Me-6-MeO-pyrid-3-yl | |
| 375 | Me | CH(Et)CH$_2$CH$_2$OMe | 2-Me-6-MeO-pyrid-3-yl | |
| 376 | Me | 3-pentyl | 2-Me-6-MeO-pyrid-3-yl | |
| 377 | Me | 2-pentyl | 2-Me-6-MeO-pyrid-3-yl | |

TABLE 1-continued

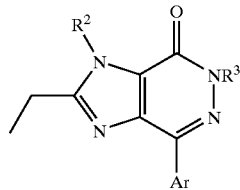

| Ex. | R₃ | R₂ | Ar | mp (° C.) |
|---|---|---|---|---|
| 378 | Me | 2-butyl | 2-Me-6-MeO-pyrid-3-yl | |
| 379 | Me | cyclobutyl | 2-Me-6-MeO-pyrid-3-yl | |
| 380 | Me | cyclopentyl | 2-Me-6-MeO-pyrid-3-yl | |
| 381 | Me | CH(Me)cyclobutyl | 2-Me-6-MeO-pyrid-3-yl | |
| 382 | Me | CH(Me)cyclopropyl | 2-Me-6-MeO-pyrid-3-yl | |
| 383 | Me | CH(Et)cyclobutyl | 2-Me-6-MeO-pyrid-3-yl | |
| 384 | Me | CH(Et)cyclopropyl | 2-Me-6-MeO-pyrid-3-yl | |
| 385 | Me | CH(Me)CH₂-cyclobutyl | 2-Me-6-MeO-pyrid-3-yl | |
| 386 | Me | CH(Me)CH₂-cyclopropyl | 2-Me-6-MeO-pyrid-3-yl | |
| 387 | Me | CH(Et)CH₂-cyclobutyl | 2-Me-6-MeO-pyrid-3-yl | |
| 388 | Me | CH(Et)CH₂-cyclopropyl | 2-Me-6-MeO-pyrid-3-yl | |
| 389 | Me | CH(CH₂OMe)cyclobutyl | 2-Me-6-MeO-pyrid-3-yl | |
| 390 | Me | CH(CH₂OMe)cyclopropyl | 2-Me-6-MeO-pyrid-3-yl | |
| 391 | Me | CH(CH₂OEt)cyclobutyl | 2-Me-6-MeO-pyrid-3-yl | |
| 392 | Me | CH(CH₂OEt)cyclopropyl | 2-Me-6-MeO-pyrid-3-yl | |
| 393 | Me | CH(cyclobutyl)₂ | 2-Me-6-MeO-pyrid-3-yl | |
| 394 | Me | CH(cyclopropyl)₂ | 2-Me-6-MeO-pyrid-3-yl | |
| 395 | Me | CH(Et)CH₂CONMe₂ | 2-Me-6-MeO-pyrid-3-yl | |
| 396 | Me | CH(Et)CH₂CH₂NMe₂ | 2-Me-6-MeO-pyrid-3-yl | |
| 397 | Me | CH(CH₂OMe)Me | 2-Me-6-MeO-pyrid-3-yl | |
| 398 | Me | CH(CH₂OMe)Et | 2-Me-6-MeO-pyrid-3-yl | |
| 399 | Me | CH(CH₂OMe)Pr | 2-Me-6-MeO-pyrid-3-yl | |
| 400 | Me | CH(CH₂OEt)Me | 2-Me-6-MeO-pyrid-3-yl | |
| 401 | Me | CH(CH₂OEt)Et | 2-Me-6-MeO-pyrid-3-yl | |
| 402 | Me | CH(CH₂OEt)Pr | 2-Me-6-MeO-pyrid-3-yl | |
| 403 | Me | CH(CH₂C≡CMe)Et | 2-Me-6-MeO-pyrid-3-yl | |
| 404 | Me | CH(CH₂CH=CHMe)Et | 2-Me-6-MeO-pyrid-3-yl | |
| 405 | Me | CH(Et)CH₂OH | 4-Me-2-MeO-pyrid-5-yl | |
| 406 | Me | CH(Et)CH₂OMe | 4-Me-2-MeO-pyrid-5-yl | |
| 407 | Me | CH(Et)CH₂CH₂OMe | 4-Me-2-MeO-pyrid-5-yl | |
| 408 | Me | 3-pentyl | 4-Me-2-MeO-pyrid-5-yl | |
| 409 | Me | 2-pentyl | 4-Me-2-MeO-pyrid-5-yl | |
| 410 | Me | 2-butyl | 4-Me-2-MeO-pyrid-5-yl | |
| 411 | Me | cyclobutyl | 4-Me-2-MeO-pyrid-5-yl | |
| 412 | Me | cyclopentyl | 4-Me-2-MeO-pyrid-5-yl | |
| 413 | Me | CH(Me)cyclobutyl | 4-Me-2-MeO-pyrid-5-yl | |
| 414 | Me | CH(Me)cyclopropyl | 4-Me-2-MeO-pyrid-5-yl | |
| 415 | Me | CH(Et)cyclobutyl | 4-Me-2-MeO-pyrid-5-yl | |
| 416 | Me | CH(Et)cyclopropyl | 4-Me-2-MeO-pyrid-5-yl | |
| 417 | Me | CH(Me)CH₂-cyclobutyl | 4-Me-2-MeO-pyrid-5-yl | |
| 418 | Me | CH(Me)CH₂-cyclopropyl | 4-Me-2-MeO-pyrid-5-yl | |
| 419 | Me | CH(Et)CH₂-cyclobutyl | 4-Me-2-MeO-pyrid-5-yl | |
| 420 | Me | CH(Et)CH₂-cyclopropyl | 4-Me-2-MeO-pyrid-5-yl | |
| 421 | Me | CH(CH₂OMe)cyclobutyl | 4-Me-2-MeO-pyrid-5-yl | |
| 422 | Me | CH(CH₂OMe)cyclopropyl | 4-Me-2-MeO-pyrid-5-yl | |
| 423 | Me | CH(CH₂OEt)cyclobutyl | 4-Me-2-MeO-pyrid-5-yl | |
| 424 | Me | CH(CH₂OEt)cyclopropyl | 4-Me-2-MeO-pyrid-5-yl | |
| 425 | Me | CH(cyclobutyl)₂ | 4-Me-2-MeO-pyrid-5-yl | |
| 426 | Me | CH(cyclopropyl)₂ | 4-Me-2-MeO-pyrid-5-yl | |
| 427 | Me | CH(Et)CH₂CONMe₂ | 4-Me-2-MeO-pyrid-5-yl | |
| 428 | Me | CH(Et)CH₂CH₂NMe₂ | 4-Me-2-MeO-pyrid-5-yl | |
| 429 | Me | CH(CH₂OMe)Me | 4-Me-2-MeO-pyrid-5-yl | |
| 430 | Me | CH(CH₂OMe)Et | 4-Me-2-MeO-pyrid-5-yl | |
| 431 | Me | CH(CH₂OMe)Pr | 4-Me-2-MeO-pyrid-5-yl | |
| 432 | Me | CH(CH₂OEt)Me | 4-Me-2-MeO-pyrid-5-yl | |
| 433 | Me | CH(CH₂OEt)Et | 4-Me-2-MeO-pyrid-5-yl | |
| 434 | Me | CH(CH₂OEt)Pr | 4-Me-2-MeO-pyrid-5-yl | |
| 435 | Me | CH(CH₂C≡CMe)Et | 4-Me-2-MeO-pyrid-5-yl | |
| 436 | Me | CH(CH₂CH=CHMe)Et | 4-Me-2-MeO-pyrid-5-yl | |
| 536 | H | 2-pentyl | 2,4-Cl₂-5-F—Ph | 159–160 |
| 537 | Me | 2-pentyl | 2,4-Cl₂-5-F—Ph | 120–121 |
| 538 | Me | (R)-2-butyl | 2,4-Cl₂—Ph | 105–107 |
| 539 | Me | (S)-2-butyl | 2,4-Cl₂—Ph | oil |
| 540 | Me | 2-pentyl | 4-Br-2-Cl—Ph | 97–98 |
| 541 | Me | 2-pentyl | Ph | oil |
| 542 | Me | 2-pentyl | 4-OMe-Ph | oil |

TABLE 1-continued

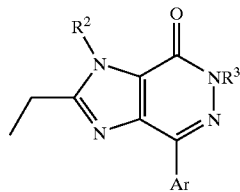

| Ex. | R₃ | R₂ | Ar | mp (° C.) |
|---|---|---|---|---|
| 543 | Me | CH₂OCH₂Ph | 2,4-Cl₂—Ph | oil |
| 544 | Me | H | 2,4-Cl₂—Ph | 234–235 |
| 545 | H | CH₂OCH₂Ph | 2,4-Cl₂—Ph | 174–175 |
| 546 | Me | n-butyl | 2,4-Cl₂—Ph | oil |
| 547 | Me | CH₂CH₂OMe | 2,4-Cl₂—Ph | oil |
| 548 | Me | 3-heptyl | 2,4-Cl₂—Ph | 110–111 |
| 549 | Me | (S)-2-pentyl | 2,4-Cl₂—Ph | oil |
| 550 | Me | (R)-2-pentyl | 2,4-Cl₂—Ph | oil |
| 551 | Me | CH(Et)CH₂C≡CH | 2,4-Cl₂—Ph | oil |
| 552 | Me | 2-hexyl | 2,4-Cl₂—Ph | oil |
| 553 | Me | 3-hexyl | 2,4-Cl₂—Ph | 135–136 |
| 554 | Me | CH(Et)CH₂CH₂CH=CH₂ | 2,4-Cl₂—Ph | 106–107 |
| 555 | Me | CH(CH₂CH=CH₂)₂ | 2,4-Cl₂—Ph | oil |
| 556 | Me | CH(Me)CH₂OCH₃ | 2,4-Cl₂—Ph | oil |
| 557 | Me | CH(n-C₃H₇)-cyclopropyl | 2,4-Cl₂—Ph | 139–140 |
| 558 | Me | CH(Ph)-cyclopropyl | 2,4-Cl₂—Ph | 172–173 |
| 559 | Me | CH(4-OMe-Ph)-cyclopropyl | 2,4-Cl₂—Ph | oil |
| 560 | Me | CH(4-Me-Ph)-cyclopropyl | 2,4-Cl₂—Ph | oil |
| 561 | Me | CH(4-F—Ph)-cyclopropyl | 2,4-Cl₂—Ph | oil |
| 562 | Me | CH₂CH(CH₃)₂ | 2,4-Cl₂—Ph | oil |
| 563 | Me | CH₂C(=CH₂)Me | 2,4-Cl₂—Ph | 126–127 |
| 564 | Me | CH₂CH₂CH(CH₃)₂ | 2,4-Cl₂—Ph | 105–106 |
| 565 | Me | CH₂CH₂CH=CH₂ | 2,4-Cl₂—Ph | oil |
| 566 | Me | CH₂C≡CMe | 2,4-Cl₂—Ph | 148–149 |
| 567 | Me | (R)-CH₂CH(Me)CH₂CH₃ | 2,4-Cl₂—Ph | oil |
| 568 | Me | (S)-CH₂CH(Me)CH₂CH₃ | 2,4-Cl₂—Ph | oil |
| 569 | Me | CH₂COCH₂CH₃ | 2,4-Cl₂—Ph | 104–105 |
| 570 | Me | CH₂CH(CH₂CH₃)₂ | 2,4-Cl₂—Ph | oil |
| 571 | Me | n-pentyl | 2,4-Cl₂—Ph | oil |
| 572 | Me | CH₂(CH₂)₂CH=CH₂ | 2,4-Cl₂—Ph | oil |
| 573 | Me | CH₂CH=CHCH₂CH₃ | 2,4-Cl₂—Ph | oil |
| 574 | Me | CH₂(2-Cl—Ph) | 2,4-Cl₂—Ph | 163–165 |
| 575 | Me | CH₂(3-Cl—Ph) | 2,4-Cl₂—Ph | 82–84 |
| 576 | Me | CH₂(4-Cl—Ph) | 2,4-Cl₂—Ph | 149–150 |
| 577 | Me | CH₂(2,4-Cl₂—Ph) | 2,4-Cl₂—Ph | 85–87 |
| 578 | Me | CH₂(2,4-F₂—Ph) | 2,4-Cl₂—Ph | oil |
| 579 | Me | CH(Me)Ph | 2,4-Cl₂—Ph | 179–180 |
| 580 | Me | CH₂CH₂Ph | 2,4-Cl₂—Ph | oil |
| 581 | Me | CH₂-cyclobutyl | 2,4-Cl₂—Ph | oil |
| 582 | Me | 2-pentyl | 2-4-CF₃—Ph | oil |
| 583 | Me | 2-pentyl | 2-Cl-4-F—Ph | oil |
| 584 | Me | 2-pentyl | 2,4-Cl₂—Ph | oil |
| 585 | Me | 2-pentyl | 2,6-(OMe)₂-pyrid-5-yl | oil |

TABLE 2

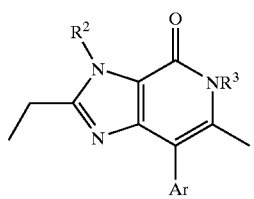

| Ex. | R₃ | R₂ | Ar | mp (° C.) |
|---|---|---|---|---|
| 437 | Me | CH(Et)CH₂OH | 2,4-Cl₂—Ph | |
| 438 | Me | CH(Et)CH₂OMe | 2,4-Cl₂—Ph | |
| 439 | Me | CH(Et)CH₂CH₂OMe | 2,4-Cl₂—Ph | |
| 440 | Me | 3-pentyl | 2,4-Cl₂—Ph | |
| 441 | Me | 2-pentyl | 2,4-Cl₂—Ph | |

TABLE 2-continued

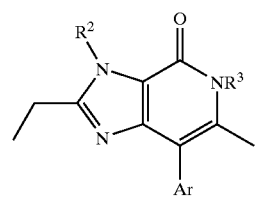

| Ex. | R₃ | R₂ | Ar | mp (° C.) |
|---|---|---|---|---|
| 442 | Me | 2-butyl | 2,4-Cl₂—Ph | |
| 443 | Me | cyclobutyl | 2,4-Cl₂—Ph | |
| 444 | Me | cyclopentyl | 2,4-Cl₂—Ph | |
| 445 | Me | CH(Me)cyclobutyl | 2,4-Cl₂—Ph | |
| 446 | Me | CH(Me)cyclopropyl | 2,4-Cl₂—Ph | |

TABLE 2-continued

Structure: 2-ethyl imidazo pyridazinone with R2 on N, NR3, Ar, and methyl group

| Ex. | R3 | R2 | Ar | mp (° C.) |
|---|---|---|---|---|
| 447 | Me | CH(Et)cyclobutyl | 2,4-Cl₂—Ph | |
| 448 | Me | CH(Et)cyclopropyl | 2,4-Cl₂—Ph | |
| 449 | Me | CH(Me)CH₂-cyclobutyl | 2,4-Cl₂—Ph | |
| 450 | Me | CH(OH)CH₂-cyclobutyl | 2,4-Cl₂—Ph | |
| 451 | Me | CH(Me)CH₂-cyclopropyl | 2,4-Cl₂—Ph | |
| 452 | Me | CH(Et)CH₂-cyclobutyl | 2,4-Cl₂—Ph | |
| 453 | Me | CH(Et)CH₂-cyclopropyl | 2,4-Cl₂—Ph | |
| 454 | Me | CH(CH₂OMe)cyclobutyl | 2,4-Cl₂—Ph | |
| 455 | Me | CH(CH₂OMe)cyclopropyl | 2,4-Cl₂—Ph | |
| 456 | Me | CH(CH₂OEt)cyclobutyl | 2,4-Cl₂—Ph | |
| 457 | Me | CH(CH₂OEt)cyclopropyl | 2,4-Cl₂—Ph | |
| 458 | Me | CH(cyclobutyl)₂ | 2,4-Cl₂—Ph | |
| 459 | Me | CH(cyclopropyl)₂ | 2,4-Cl₂—Ph | |
| 460 | Me | CH(Et)CH₂CONMe₂ | 2,4-Cl₂—Ph | |
| 461 | Me | CH(Et)CH₂NMe₂ | 2,4-Cl₂—Ph | |
| 462 | Me | CH(CH₂OMe)Me | 2,4-Cl₂—Ph | |
| 463 | Me | CH(CH₂OMe)Et | 2,4-Cl₂—Ph | |
| 464 | Me | CH(CH₂OMe)Pr | 2,4-Cl₂—Ph | |
| 465 | Me | CH(CH₂OEt)Me | 2,4-Cl₂—Ph | |
| 466 | Me | CH(CH₂OEt)Et | 2,4-Cl₂—Ph | |
| 467 | Me | CH(CH₂OEt)Pr | 2,4-Cl₂—Ph | |
| 468 | Me | CH(CH₂C≡CMe)Et | 2,4-Cl₂—Ph | |
| 469 | Me | CH(CH₂CH=CHMe)Et | 2,4-Cl₂—Ph | |

TABLE 3

Structure: 2-methoxy imidazo pyridazinone

| Ex. | R3 | R2 | Ar | mp (° C.) |
|---|---|---|---|---|
| 470 | Me | CH(Et)CH₂OH | 2,4-Cl₂—Ph | |
| 471 | Me | CH(Et)CH₂OMe | 2,4-Cl₂—Ph | |
| 472 | Me | CH(Et)CH₂CH₂OMe | 2,4-Cl₂—Ph | |
| 473 | Me | 3-pentyl | 2,4-Cl₂—Ph | |
| 474 | Me | 2-pentyl | 2,4-Cl₂—Ph | |
| 475 | Me | 2-butyl | 2,4-Cl₂—Ph | |
| 476 | Me | cyclobutyl | 2,4-Cl₂—Ph | |
| 477 | Me | cyclopentyl | 2,4-Cl₂—Ph | |
| 478 | Me | CH(Me)cyclobutyl | 2,4-Cl₂—Ph | |
| 479 | Me | CH(Me)cyclopropyl | 2,4-Cl₂—Ph | |
| 480 | Me | CH(Et)cyclobutyl | 2,4-Cl₂—Ph | |
| 481 | Me | CH(Et)cyclopropyl | 2,4-Cl₂—Ph | |
| 482 | Me | CH(Me)CH₂-cyclobutyl | 2,4-Cl₂—Ph | |
| 483 | Me | CH(OH)CH₂-cyclobutyl | 2,4-Cl₂—Ph | |
| 484 | Me | CH(Me)CH₂-cyclopropyl | 2,4-Cl₂—Ph | |
| 485 | Me | CH(Et)CH₂-cyclobutyl | 2,4-Cl₂—Ph | |
| 486 | Me | CH(Et)CH₂-cyclopropyl | 2,4-Cl₂—Ph | |
| 487 | Me | CH(CH₂OMe)cyclobutyl | 2,4-Cl₂—Ph | |
| 488 | Me | CH(CH₂OMe)cyclopropyl | 2,4-Cl₂—Ph | |
| 489 | Me | CH(CH₂OEt)cyclobutyl | 2,4-Cl₂—Ph | |
| 490 | Me | CH(CH₂OEt)cyclopropyl | 2,4-Cl₂—Ph | |
| 491 | Me | CH(cyclobutyl)₂ | 2,4-Cl₂—Ph | |
| 492 | Me | CH(cyclopropyl)₂ | 2,4-Cl₂—Ph | |

TABLE 3-continued

| Ex. | R3 | R2 | Ar | mp (° C.) |
|---|---|---|---|---|
| 493 | Me | CH(Et)CH₂CONMe₂ | 2,4-Cl₂—Ph | |
| 494 | Me | CH(Et)CH₂CH₂NMe₂ | 2,4-Cl₂—Ph | |
| 495 | Me | CH(CH₂OMe)Me | 2,4-Cl₂—Ph | |
| 496 | Me | CH(CH₂OMe)Et | 2,4-Cl₂—Ph | |
| 497 | Me | CH(CH₂OMe)Pr | 2,4-Cl₂—Ph | |
| 498 | Me | CH(CH₂OEt)Me | 2,4-Cl₂—Ph | |
| 499 | Me | CH(CH₂OEt)Et | 2,4-Cl₂—Ph | |
| 500 | Me | CH(CH₂OEt)Pr | 2,4-Cl₂—Ph | |
| 501 | Me | CH(CH₂C≡CMe)Et | 2,4-Cl₂—Ph | |
| 502 | Me | CH(CH₂C≡CMe)Et | 2,4-Cl₂—Ph | |

TABLE 4

Structure: 2-methoxy imidazo pyridinone with methyl

| Ex. | R3 | R2 | Ar | mp (° C.) |
|---|---|---|---|---|
| 503 | Me | CH(Et)CH₂OH | 2,4-Cl₂—Ph | |
| 504 | Me | CH(Et)CH₂OMe | 2,4-Cl₂—Ph | |
| 505 | Me | CH(Et)CH₂CH₂OMe | 2,4-Cl₂—Ph | |
| 506 | Me | 3-pentyl | 2,4-Cl₂—Ph | |
| 507 | Me | 2-pentyl | 2,4-Cl₂—Ph | |
| 508 | Me | 2-butyl | 2,4-Cl₂—Ph | |
| 509 | Me | cyclobutyl | 2,4-Cl₂—Ph | |
| 510 | Me | cyclopentyl | 2,4-Cl₂—Ph | |
| 511 | Me | CH(Me)cyclobutyl | 2,4-Cl₂—Ph | |
| 512 | Me | CH(Me)cyclopropyl | 2,4-Cl₂—Ph | |
| 513 | Me | CH(Et)cyclobutyl | 2,4-Cl₂—Ph | |
| 514 | Me | CH(Et)cyclopropyl | 2,4-Cl₂—Ph | |
| 515 | Me | CH(Me)CH₂-cyclobutyl | 2,4-Cl₂—Ph | |
| 516 | Me | CH(OH)CH₂-cyclobutyl | 2,4-Cl₂—Ph | |
| 517 | Me | CH(Me)CH₂-cyclopropyl | 2,4-Cl₂—Ph | |
| 518 | Me | CH(Et)CH₂-cyclobutyl | 2,4-Cl₂—Ph | |
| 519 | Me | CH(Et)CH₂-cyclopropyl | 2,4-Cl₂—Ph | |
| 520 | Me | CH(CH₂OMe)cyclobutyl | 2,4-Cl₂—Ph | |
| 521 | Me | CH(CH₂OMe)cyclopropyl | 2,4-Cl₂—Ph | |
| 522 | Me | CH(CH₂OEt)cyclobutyl | 2,4-Cl₂—Ph | |
| 523 | Me | CH(CH₂OEt)cyclopropyl | 2,4-Cl₂—Ph | |
| 524 | Me | CH(cyclobutyl)₂ | 2,4-Cl₂—Ph | |
| 525 | Me | CH(cyclopropyl)₂ | 2,4-Cl₂—Ph | |
| 526 | Me | CH(Et)CH₂CONMe₂ | 2,4-Cl₂—Ph | |
| 527 | Me | CH(Et)CH₂CH₂NMe₂ | 2,4-Cl₂—Ph | |
| 528 | Me | CH(CH₂OMe)Me | 2,4-Cl₂—Ph | |
| 529 | Me | CH(CH₂OMe)Et | 2,4-Cl₂—Ph | |
| 530 | Me | CH(CH₂OMe)Pr | 2,4-Cl₂—Ph | |
| 531 | Me | CH(CH₂OEt)Me | 2,4-Cl₂—Ph | |
| 532 | Me | CH(CH₂OEt)Et | 2,4-Cl₂—Ph | |
| 533 | Me | CH(CH₂OEt)Pr | 2,4-Cl₂—Ph | |
| 534 | Me | CH(CH₂C≡CMe)Et | 2,4-Cl₂—Ph | |
| 535 | Me | CH(CH₂CH=CHMe)Et | 2,4-Cl₂—Ph | |

Examples shown above in Tables 1–4 wherein R³ is H, C₂H₅, C₃H₇ or C₁₋₆alkylC₃₋₆ cycloalkyl are also readily prepared according to the procedures disclosed herein.

CRF Receptor Binding Assay for the Evaluation of Biological Activity

Radioligand Binding Experiments

Compounds of the invention were tested for in vitro activity as CRF receptor antagonists. The tests described below demonstrated that the examples tested had $K_i$s of 10,000 nM or less and are thus useful as CRF receptor antagonists. Preferred antagonists have or will have a $K_i$ of 1,000 nM or less. Radioligand binding experiments were performed with membranes from rat frontal cortex to determine binding affinities ($K_i$'s) of test compounds for the rat $CRH_1$ receptor using a modified version of methods described earlier (see E. B. DeSouza, J. Neurosci, 7:88, 1987). Rat cortex was homogenized in tissue buffer (containing 50 mM HEPES, 10 mM $MgCl_2$, 2 mM EGTA, and 1 μg/ml each of aprotonin, leupeptin, and pepstatin, pH 7.0 @ 23° C.) using a Brinkman Polytron (PT-10, setting 6 for 10 sec). The homogenate was centrifuged at 48,000×g for 12 min and the resulting pellet was washed by two sequential re-suspension and centrifugation steps. The final pellet was suspended to tissue buffer to a working concentration of 0.1 mg/ml protein. Protein determinations were made using the bicinchoninic acid (BCA) assay (Pierce, Rockford, Ill.) with bovine serum albumin as the standard.

All test compounds were prepared in assay buffer, which was identical to the tissue buffer except for the inclusion of 0.15 mM bacitracin and 0.1% w/v ovalbumin. Binding assay were conducted in disposable polypropylene 96-well plates (Costar Corp., Cambridge, Mass.) and initiated by the addition of 100 μl membrane homogenate (containing 40–60 μg protein) to 200 μl of assay buffer containing radioligands (150 pM, final concentration, [$^{125}$I] tyr° ovine CRH; New England Nuclear, MA) and competing test compounds. Specific binding was determined in the presence of 10 μM α-helical CRH. Competition experiments were conducted using 12 concentrations of ligand (ranging from $1\times10^{-11}$ to $1\times10^{-5}$ M). The reactions mixtures were incubated to equilibrium for 2 hr at 23° C. and terminated by rapid filtration using a cell harvester (Inotech Biosystems Inc., Lansing Mich.) over GFF glass-fibers (pre-soaked in 0.3% v/v polyethyleneimine). Filters were rapidly washed 3× with 0.3 ml cold wash buffer (PBS, pH 7.0, containing 0.01% Triton X-100), dried, and counted in a gamma counter at 80% efficiency.

Binding affinities ($K_i$'s) of ligands for the $CRH_1$ receptor were calculated using the iterative nonlinear regression curve-fitting programs (LIGAND) of Munson and Rodbard (Anal. Biochem. 1980, 107, 220–239) or Prism (GraphPad Prism, San Diego, Calif.). Data were best-fit by the one-site/state competition equation.

Inhibition of CRF-Stimulated Adenylate Cyclase Activity

Inhibition of CRF-stimulated adenylate cyclase activity can be performed as described by G. Battaglia et al. Synapse 1:572 (1987). Briefly, assays are carried out at 37° C. for 10 min in 200 ml of buffer containing 100 mM Tris-HCl (pH 7.4 at 37° C.), 10 mM $MgCl_2$, 0.4 mM EGTA, 0.1% BSA, 1 mM isobutylmethylxanthine (IBMX), 250 units/ml phosphocreatine kinase, 5 mM creatine phosphate, 100 mM guanosine 5'-triphosphate, 100 nM OCRF, antagonist peptides (concentration range $10^{-9}$ to $10^{-6m}$) and 0.8 mg original wet weight tissue (approximately 40–60 mg protein). Reactions are initiated by the addition of 1 mM ATP/$^{32}$P] ATP (approximately 2–4 mCi/tube) and terminated by the addition of 100 ml of 50 mM Tris-HCL, 45 mM ATP and 2% sodium dodecyl sulfate. In order to monitor the recovery of cAMP, 1 μl of [$^3$H]cAMP (approximately 40,000 dpm) is added to each tube prior to separation. The separation of [$^{32}$P]cAMP from [$^{32}$P]ATP is performed by sequential elution over Dowex and alumina columns.

In vivo Biological Assay

The in vivo activity of the compounds of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn *Brain Research Reviews* 15:71 (1990). Compounds may be tested in any species of rodent or small mammal.

Compounds of this invention have utility in the treatment of inbalances associated with abnormal levels of corticotropin releasing factor in patients suffering from depression, affective disorders, and/or anxiety.

Compounds of this invention can be administered to treat these abnormalities by means that produce contact of the active agent with the agent's site of action in the body of a mammal. The compounds can be administered by any conventional means available for use in conjunction with pharmaceuticals either as individual therapeutic agent or in combination of therapeutic agents. They can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally is solid dosage forms, such as capsules, tablets and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can contain coloring or flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in the field.

Useful pharmaceutical dosage-forms for administration of the compounds of this invention can be illustrated as follows:

Capsules

A large number of units capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules were washed and dried.

Tablets

A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

The compounds of this invention may also be used as reagents or standards in the biochemical study of neurological function, dysfunction, and disease.

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:

1. A compound of Formula (1):

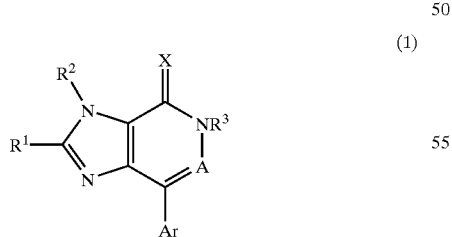

(1)

or geometric isomers thereof, stereoisomeric forms thereof, or mixtures of stereoisomeric forms thereof, or pharmaceutically acceptable salt or pro-drug forms thereof, wherein:

X is O or S;

A=N;

Ar is selected from phenyl, naphthyl, pyridyl, pyrimidinyl, triazinyl, furanyl, thienyl, benzothienyl, benzofuranyl, 2,3-dihydrobenzofuranyl, 2,3-dihydrobenzothienyl, indanyl, 1,2-benzopyranyl, 3,4-dihydro-1,2-benzopyranyl, tetralinyl, each Ar optionally substituted with 1 to 5 $R^4$ groups and each Ar is attached via an unsaturated carbon atom;

$R^1$ is independently selected at each occurrence from H, $C_1$–$C_4$ alkyl, $C_2$–$C_4$ alkenyl, $C_2$–$C_4$ alkynyl, halo, CN, $C_1$–$C_4$ haloalkyl, $C_1$–$C_{12}$ hydroxyalkyl, $C_2$–$C_{12}$ alkoxyalkyl, $C_2$–$C_{10}$ cyanoalkyl, $C_3$–$C_6$ cycloalkyl, $C_4$–$C_{10}$ cycloalkylalkyl, $NR^9R^{10}$, $C_1$–$C_4$ alkyl-$NR^9R^{10}$, $NR^9COR^{10}$, $OR^{11}$, SH or $S(O)_nR^{12}$;

$R^2$ is selected from:
—H, aryl, heteroaryl and heterocyclyl, or
—$C_1$–$C_{10}$ alkyl, $C_2$–$C_{10}$ alkenyl, $C_2$–$C_{10}$ alkynyl, $C_3$–$C_8$ cycloalkyl, $C_5$–$C_8$ cycloalkenyl, $C_4$–$C_{12}$ cycloalkylalkyl or $C_6$–$C_{10}$ cycloalkenylalkyl, each optionally substituted with 1 to 3 substituents independently selected at each occurrence from $C_1$–$C_6$ alkyl, $C_{1-6}$ alkyloxy-$C_{1-6}$ alkyl, $C_{2-6}$ alkenyl, $C_{2-6}$ alkynyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl and heterocyclyl;

$R^3$ is selected from:
—H, aryl, heteroaryl and heterocyclyl, or
$C_1$–$C_4$ alkyl, $C_3$–$C_6$ alkenyl, $C_3$–$C_6$ alkynyl, $C_3$–$C_6$ cycloalkyl, $C_4$–$C_{10}$ cycloalkylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{123}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl and heterocyclyl;

$R^4$ is independently selected at each occurrence from:
$C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, $NO_2$, halo, CN, $C_1$–$C_4$ haloalkyl, $NR^6R^7$, $NR^6COR^7$, $NR^6CO_2R^7$, $COR^7$, $OR^7$, $CONR^6R^7$, $CO(NOR^9)R^7$, $CO_2R^7$, or $S(O)_nR^7$, where each such $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, $NO_2$, halo, CN, $NR^6R^7$, $NR^6COR^7$, $NR^6CO_2R^7$, $COR^7$ $OR^7$, $CONR^6R^7$, $CO_2R^7$, $CO(NOR^9)R^7$, or $S(O)_nR^7$;

$R^6$ and $R^7$ are independently selected at each occurrence from:
—H,
—$C_1$–$C_{10}$ alkyl, $C_3$–$C_{10}$ alkenyl, $C_3$–$C_{10}$ alkynyl, $C_1$–$C_{10}$ haloalkyl with 1–10 halogens, $C_2$–$C_8$ alkoxyalkyl, $C_3$–$C_6$ cycloalkyl, $C_4$–$C_{12}$ cycloalkylalkyl, $C_5$–$C_{10}$ cycloalkenyl, or $C_6$–$C_{14}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl,
-aryl, aryl($C_1$–$C_4$ alkyl), heteroaryl, heteroaryl($C_1$–$C_4$ alkyl), heterocyclyl or heterocyclyl($C_1$–$C_4$ alkyl);

alternatively, $NR^6R^7$ is piperidine, pyrrolidine, piperazine, N-methylpiperazine, morpholine or thiomorpholine, each optionally substituted with 1–3 $C_1$–$C_4$ alkyl groups;

$R^8$ is independently selected at each occurrence from H or $C_1$–$C_4$ alkyl optionally substituted by halogen, $C_1$–$C_4$ alkoxy or $C_1$–$C_4$ halo-alkoxy (1 to 4 halogens);

$R^9$ and $R^{10}$ are independently selected at each occurrence from H, $C_1$–$C_4$ alkyl, or $C_3$–$C_6$ cycloalkyl;

$R^{11}$ is selected from H, $C_1$–$C_4$ alkyl, $C_1$–$C_4$ haloalkyl, or $C_3$–$C_6$ cycloalkyl;

$R^{12}$ is $C_1$–$C_4$ alkyl or $C_1$–$C_4$ haloalkyl;

$R^{13}$ is selected from $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl)-;

$R^{15}$ and $R^{16}$ are independently selected at each occurrence from H, $C_1$–$C_6$ alkyl, $C_3$–$C_{10}$ cycloalkyl, $C_4$–$C_{16}$ cycloalkylalkyl, except that for $S(O)_nR^{15}$, $R^{15}$ cannot be H;

aryl is phenyl or naphthyl, each optionally substituted with 1 to 5 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{15}$, $COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$, $NR^{16}R^{15}$, and $CONR^{16}R^{15}$;

heteroaryl is pyridyl, pyrimidinyl, triazinyl, furanyl, pyranyl, quinolinyl, isoquinolinyl, thienyl, imidazolyl, thiazolyl, indolyl, pyrrolyl, oxazolyl, benzofuranyl, benzothienyl, benzothiazolyl, isoxazolyl, pyrazolyl, 2,3-dihydrobenzothienyl or 2,3-dihydrobenzofuranyl, each being optionally substituted with 1 to 5 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{15}$, —$COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$, $NR^{16}R^{15}$, and $CONR^{16}R^{15}$;

heterocyclyl is saturated or partially saturated heteroaryl, optionally substituted with 1 to 5 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{15}$, $COR^{15}$, $C_2R^{15}$, $OC(O)R^{15}$, $NR^8COR^{15}$, $N(COR^{15})_2$, $NR^8CONR^{16}R^{15}$, $NR^8CO_2R^{15}$, $NR^{15}R^{16}$, and $CONR^{16}R^{15}$; and n is independently at each occurrence 0, 1 or 2.

2. The compound according to claim 1 wherein Ar is phenyl or pyridyl, each optionally substituted with 1 to 4 $R^4$ substituents.

3. The compound according to claim 1 wherein Ar is phenyl wherein phenyl is optionally substituted with 1 to 3 $R^4$ substituents.

4. The compound according to claim 1 wherein $R^2$ is:
—$C_1$–$C_{10}$ alkyl, $C_2$–$C_{10}$ alkenyl, $C_2$–$C_{10}$ alkynyl, $C_3$–$C_8$ cycloalkyl, $C_5$–$C_8$ cycloalkenyl, $C_4$–$C_{12}$ cycloalkylalkyl or $C_6$–$C_{10}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl and heterocyclyl.

5. The compound according to claim 1 wherein $R^1$, $R^2$ and $R^3$ are independently selected from $C_{1-6}$ alkyl or $C_{1-6}$ alkyloxy.

6. A pharmaceutical composition comprising the compound of claim 1 and a pharmaceutically acceptable carrier.

7. A method of antagonizing a CRF receptor in a mammal comprising contacting the receptor with a compound of the formula:

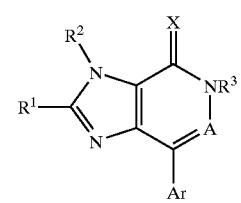

(1)

or geometric isomers thereof, stereoisomeric forms thereof, or mixtures of stereoisomeric forms thereof, or pharmaceutically acceptable salt or pro-drug forms thereof, wherein:

X is O or S;

A=N;

Ar is selected from phenyl, naphthyl, pyridyl, pyrimidinyl, triazinyl, furanyl, thienyl, benzothienyl, benzofuranyl, 2,3-dihydrobenzofuranyl, 2,3-dihydrobenzothienyl, indanyl, 1,2-benzopyranyl, 3,4-dihydro-1,2-benzopyranyl, tetralinyl, each Ar optionally substituted with 1 to 5 $R^4$ groups and each Ar is attached via an unsaturated carbon atom;

$R^1$ is independently selected at each occurrence from H, $C_1$–$C_4$ alkyl, $C_2$–$C_4$ alkenyl, $C_2$–$C_4$ alkynyl, halo, CN, $C_1$–$C_4$ haloalkyl, $C_1$–$C_{12}$ hydroxyalkyl, $C_2$–$C_{12}$ alkoxyalkyl, $C_2$–$C_{10}$ cyanoalkyl, $C_3$–$C_6$ cycloalkyl, $C_4$–$C_{10}$ cycloalkylalkyl, $NR^9R^{10}$, $C_1$–$C_4$ alkyl-$NR^9R^{10}$, $NR^9COR^{10}$, $OR^{11}$, SH or $S(O)_nR^{12}$;

$R^2$ is selected from:
—H, aryl, heteroaryl and heterocyclyl, or
—$C_{10}$ alkyl, $C_2$–$C_{10}$ alkenyl, $C_2$–$C_{10}$ alkynyl, $C_3$–$C_8$ cycloalkyl, $C_5$–$C_8$ cycloalkenyl, $C_4$–$C_{12}$ cycloalkylalkyl or $C_6$–$C_{10}$ cycloalkenylalkyl, each optionally substituted with 1 to 3 substituents independently selected at each occurrence from $C_1$–$C_6$ alkyl, $C_{1-6}$ alkyloxy $C_{1-6}$ alkyl, $C_{2-6}$ alkenyl, $C_{2-6}$ alkynyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl and heterocyclyl;

$R^3$ is selected from H, $C_1$–$C_4$ alkyl, $C_3$–$C_6$ alkenyl, $C_3$–$C_6$ alkynyl, $C_3$–$C_6$ cycloalkyl, $C_4$–$C_{10}$ cycloalkylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl and heterocyclyl;

$R^4$ is independently selected at each occurrence from:
$C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, $NO_2$, halo, CN, $C_1$–$C_4$ haloalkyl, $NR^6R^7$, $NR^6COR^7$, $NR^6CO_2R^7$, $COR^7$, $OR^7$, $CONR^6R^7$, $CO(NOR^9)R^7$, $CO_2R^7$, or $S(O)_nR^7$, where each such $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, $NO_2$, halo, CN, $NR^6R^7$, $NR^6COR^7$, $NR^6CO_2R^7$, $COR^7$ $OR^7$, $CONR^6R^7$, $CO_2R^7$, $CO(NOR^9)R^7$, or $S(O)_nR^7$;

$R^6$ and $R^7$ are independently selected at each occurrence from:
- —H,
- —$C_1$–$C_{10}$ alkyl, $C_3$–$C_{10}$ alkenyl, $C_3$–$C_{10}$ alkynyl, $C_1$–$C_{10}$ haloalkyl with 1–10 halogens, $C_2$–$C_8$ alkoxyalkyl, $C_3$–$C_6$ cycloalkyl, $C_4$–$C_{12}$ cycloalkylalkyl, $C_5$–$C_{10}$ cycloalkenyl, or $C_6$–$C_{14}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl,
- -aryl, aryl($C_1$–$C_4$ alkyl), heteroaryl, heteroaryl($C_1$–$C_4$ alkyl), heterocyclyl or heterocyclyl($C_1$–$C_4$ alkyl);

alternatively, $NR^6R^7$ is piperidine, pyrrolidine, piperazine, N-methylpiperazine, morpholine or thiomorpholine, each optionally substituted with 1–3 $C_1$–$C_4$ alkyl groups;

$R^8$ is independently selected at each occurrence from H or $C_1$–$C_4$ alkyl optionally substituted by halogen, $C_1$–$C_4$ alkoxy or $C_1$–$C_4$ halo-alkoxy (1 to 4 halogens);

$R^9$ and $R^{10}$ are independently selected at each occurrence from H, $C_1$–$C_4$ alkyl, or $C_3$–$C_6$ cycloalkyl;

$R^{11}$ is selected from H, $C_1$–$C_4$ alkyl, $C_1$–$C_4$ haloalkyl, or $C_3$–$C_6$ cycloalkyl;

$R^{12}$ is $C_1$–$C_4$ alkyl or $C_1$–$C_4$ haloalkyl;

$R^{13}$ is selected from $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl)-;

$R^{15}$ and $R^{16}$ are independently selected at each occurrence from H, $C_1$–$C_6$ alkyl, $C_3$–$C_{10}$ cycloalkyl, $C_4$–$C_{16}$ cycloalkylalkyl, except that for $S(O)_nR^{15}$, $R^{15}$ cannot be H;

aryl is phenyl or naphthyl, each optionally substituted with 1 to 5 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{15}$, $COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$, $NR^{16}R^{15}$, and $CONR^{16}R^{15}$;

heteroaryl is pyridyl, pyrimidinyl, triazinyl, furanyl, pyranyl, quinolinyl, isoquinolinyl, thienyl, imidazolyl, thiazolyl, indolyl, pyrrolyl, oxazolyl, benzofuranyl, benzothienyl, benzothiazolyl, isoxazolyl, pyrazolyl, 2,3-dihydrobenzothienyl or 2,3-dihydrobenzofuranyl, each being optionally substituted with 1 to 5 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{15}$, —$COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$, $NR^{16}R^{15}$, and $CONR^{16}R^{15}$;

heterocyclyl is saturated or partially saturated heteroaryl, optionally substituted with 1 to 5 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{15}$, $COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$, $NR^{15}R^{16}$, and $CONR^{16}R^{15}$; and n is independently at each occurrence 0, 1 or 2.

8. The method according to claim 7 wherein Ar is phenyl or pyridyl, each optionally substituted with 1 to 4 $R^4$ substituents.

9. The method according to claim 7 wherein Ar is phenyl wherein the phenyl is optionally substituted with 1 to 3 $R^4$ substituents.

10. The method according to claim 7 wherein $R^2$ is:
- —$C_1$–$C_{10}$ alkyl, $C_2$–$C_{10}$ alkenyl, $C_2$–$C_{10}$ alkynyl, $C_3$–$C_8$ cycloalkyl, $C_5$–$C_8$ cycloalkenyl, $C_4$–$C_{12}$ cycloalkylalkyl or $C_6$–$C_{10}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl and heterocyclyl.

11. The method according to claim 7 wherein $R^1$, $R^2$ and $R^3$ are independently selected from $C_{1-6}$ alkyl or $C_{1-6}$ alkyloxy.

12. The method of claim 7 for treating affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated by antagonizing CRF.

13. The method of claim 7 for treating affective disorder, anxiety, depression, anorexia nervosa, drug or alcohol withdrawal symptoms, inflammatory diseases, stroke, or epilepsy.

* * * * *